United States Patent
Kumaran et al.

(10) Patent No.: US 11,339,412 B2
(45) Date of Patent: *May 24, 2022

(54) METABOLIC ENGINEERING FOR MICROBIAL PRODUCTION OF TERPENOID PRODUCTS

(71) Applicant: Manus Bio, Inc., Cambridge, MA (US)

(72) Inventors: Ajikumar Parayil Kumaran, Watertown, MA (US); Chin-Giaw Lim, Allston, MA (US); Souvik Ghosh, Walnut Creek, CA (US); Christopher Pirie, Seattle, WA (US); Jason Donald, Lexington, MA (US); Aaron Love, Boston, MA (US); Hong Nan, Daly City, CA (US); Hsien-Chung Tseng, Cambridge, MA (US); Christine Nicole S. Santos, Newton, MA (US); Ryan Philippe, Somerville, MA (US)

(73) Assignee: Manus Bio Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/862,209

(22) Filed: Apr. 29, 2020

(65) Prior Publication Data
US 2020/0299735 A1   Sep. 24, 2020

Related U.S. Application Data

(63) Continuation of application No. 15/888,573, filed on Feb. 5, 2018, now Pat. No. 10,662,442.

(60) Provisional application No. 62/454,121, filed on Feb. 3, 2017.

(51) Int. Cl.
| | | |
|---|---|---|
| C12P 5/00 | (2006.01) | |
| C12N 9/02 | (2006.01) | |
| C12N 9/04 | (2006.01) | |
| C12N 9/10 | (2006.01) | |
| C12P 7/40 | (2006.01) | |
| C12P 7/26 | (2006.01) | |
| C12P 7/02 | (2006.01) | |
| C12P 17/02 | (2006.01) | |

(52) U.S. Cl.
CPC .......... *C12P 5/007* (2013.01); *C12N 9/0006* (2013.01); *C12N 9/0093* (2013.01); *C12N 9/1085* (2013.01); *C12Y 101/01267* (2013.01); *C12Y 117/07001* (2013.01); *C12Y 205/0109* (2013.01); *C12P 7/02* (2013.01); *C12P 7/26* (2013.01); *C12P 7/40* (2013.01); *C12P 17/02* (2013.01)

(58) Field of Classification Search
None
See application file for complete search history.

(56) References Cited

U.S. PATENT DOCUMENTS

| | | | | |
|---|---|---|---|---|
| 7,297,509 | B2* | 11/2007 | Bacher | A61P 31/04 435/32 |
| 8,507,235 | B2* | 8/2013 | Chotani | C12P 5/007 435/167 |
| 8,512,988 | B2 | 8/2013 | Ajikumar et al. | |
| 8,927,241 | B2 | 1/2015 | Ajikumar et al. | |
| 9,284,570 | B2 | 3/2016 | Stephanopoulos et al. | |
| 9,359,624 | B2 | 7/2016 | Ajikumar et al. | |
| 9,404,130 | B2 | 8/2016 | Ajikumar et al. | |
| 9,796,980 | B2 | 10/2017 | Ajikumar et al. | |
| 9,957,527 | B2 | 5/2018 | Ajikumar et al. | |
| 10,662,442 | B2* | 5/2020 | Kumaran | C12Y 117/07001 |
| 2014/0162337 | A1 | 6/2014 | Chotani et al. | |
| 2015/0044747 | A1 | 2/2015 | Chou et al. | |
| 2015/0152446 | A1* | 6/2015 | Aji | C12Q 1/689 435/78 |
| 2015/0225754 | A1 | 8/2015 | Tange et al. | |

FOREIGN PATENT DOCUMENTS

| | | |
|---|---|---|
| EP | 1987147 B1 | 7/2010 |
| WO | 2010/148150 | 12/2010 |
| WO | 2015/189428 | 12/2015 |
| WO | 2015189428 A1 | 12/2015 |
| WO | 2016029153 A1 | 2/2016 |
| WO | 2016073740 A1 | 5/2016 |
| WO | 2017034942 | 3/2017 |
| WO | 2017142993 | 8/2017 |

OTHER PUBLICATIONS

Li et al. 2015 (Modification of targets related to the Entner-Doudoroff/pentose phosphate pathway route for methyl-D-erythritol-4-phosphate-dependent carotenoid biosynthesis in *Escherichia coli*; Microb. Cell Fact 14:117). (Year: 2015).*

Schwartz et al. 2001 (IscR, an Fe-S cluster-contining transcipriotn factor, represses expression of *Escherichia coli* genes encoding Fe—S cluster assembly proteins; PNAS 98(26):14895-14900). (Year: 2001).*

Ferella et al. 2006 (A solanesyl-diphosphate synthase localizes in glycosomes of Trypanosoma cruzi; J Biological Chemistry 281(51):39339-39348). (Year: 2006).*

Porcheron et al. 2014 (The small RNA RybB contributes to Siderophore production and virulence of Uropathogenic *Escherichia coli*; Infection and Immunity 82(12): 5056-5068). (Year: 2014).*

Bentley et al. "Heterologous Expression of the Mevalonic Acid Pathway in Cyanobacteria Enhances Endogenous Carbon Partitioning to Isoprene," Molecular Plant, 2014, vol. 7, No. 1, pp. 71-86.

(Continued)

*Primary Examiner* — Mary Maille Lyons
(74) *Attorney, Agent, or Firm* — Morgan, Lewis & Bockius LLP

(57) ABSTRACT

In various aspects and embodiments, the invention relates to bacterial strains and methods for making terpene and terpenoid products. The invention provides bacterial strains with improved carbon flux through the MEP pathway, to thereby increase terpene and/or terpenoid product yield by fermentation with carbon sources such as glucose.

18 Claims, 16 Drawing Sheets

Specification includes a Sequence Listing.

(56) References Cited

OTHER PUBLICATIONS

Chou et al. "Synthetic Pathway for Production of Five-Carbon Alcohols from Isopentenyl Diphosphate," Applied and Environmental Microbiology, 2012, vol. 78, No. 22, pp. 7849-7855.
International Search Report, for International Application No. PCT/US2018/016848, dated Apr. 23, 2018, 11 pages.
International Search Report, for International Application No. PCT/US2018/015527, dated May 2, 2018, 12 pages.
Zhou et al. "Metabolite Profiling Identified Methylerythritol Cyclodiphosphate Efflux as a Limiting Step in Microbial soprenoid Production," PloS One, 2012, vol. 7 No. 1, pp. 1-9.
Morrone et al. 2010 (Increasing diterpene yield with a modular metabolic engineering system in *E.coli*: comparison of MEV and MEP isoprenoid precursor pathway engineering; Appl Microbial Biotechnol 85: 1893-1906).
Zhao et al. 2013 (Methylerythritol Phosphate Pathway of Isoprenoid Biosynthesis; Annu Rev Biochem 82:497-530).
Ajikumar et al. 2010 (Isoprenoid Pathway Optimization for Taxol Precursor Overproduction in *Escherichia coli*; Science 330: 70-74).
Gao et al. 2016 (Engineering the Methylerythritol Phosphate pathway in cyanobacteria for photosynthetic isoprene production from CO2; Energy and Environmental Science 9:1400-1411).
Li et al., "Balanced activation of IspG and IspH to eliminate MEP intermediate accumulation and improve isoprenoids production in *Escherichia coli*", Metabolic Engineering, vol. 44, Aug. 31, 2017 (Aug. 31, 2017), pp. 13-21.
Zhou et al., "Metabolite Profiling Identified Methylerythritol Cyclodiphosphate Efflux as a Limiting Step in Microbial soprenoid Production", PLOS ONE, vol. 7, No. 11, Nov. 2, 2012 Nov. 2, 2012), p. e47513.
Puan et al., fldA is an essential gene required in the 2-C-methyl-D-erythritol 4-phosphate pathway for isoprenoid biosynthesis, FEBS Letters, Elsevier, Amsterdam, NL, vol. 579, No. 17, Jul. 4, 2005 (Jul. 4, 2005), pp. 3802-3806.
Withers et al., "Identification of Isopentenol Biosynthetic Genes from Bacillus subtilis by a Screening Method Based an Isoprenoid Precursor Toxicity", Applied and Environmental Microbiology, American Society for Microbiology, US, vol. 73, No. 19, Oct. 1, 2007 (Oct. 1, 2007), pp. 6277-6283.
Liu et al., "MEP pathway-mediated isopentenol production in metabolically engineered *Escherichia coli*", Microbial Cell Factories,, vol. 13, No. 1, Sep. 12, 2014 (Sep. 12, 2014), p. 135.
Ge et al., "Two unexpected promiscuous activities of the iron-sulfur protein IspH in production of isoprene and soamylene", Microbial Cell Factories, vol. 15, No. 1, May 11, 2016 (May 11, 2016), pp. 1-11.
Rohmer et al., "Isoprenoid Biosynthesis in Bacteria: a Novel Pathway for the Early Steps Leading To Isopentenyl Diphosphate", Biochemical Journal, Published By Portland Press on Behalf of the Biochemical Society, vol. 295, No. 2, Jan. 1, 1993 (Jan. 1, 1993), pp. 517-524.
Kainou et al., "Dimer Formation of Octaprenyl-diphosphate Synthase (IspB) Is Essential for Chain Length Determination of Ubiquinone", Journal of Biological Chemistry, American Society for Biochemistry and Molecular Biology, US, vol. 276, No. 11, Mar. 16, 2001 (Mar. 16, 2001), pp. 7876-7883.
Lee et al., "Biosynthesis of Isoprenoids: Crystal Structure of the [4Fe—4S] Cluster Protein IspG", Journal of Molecular Biology, Academic Press, United Kingdom, vol. 404, No. 4, Dec. 10, 2010 (Dec. 10, 2010), pp. 600-610.
Mandin et al., "A Regulatory Circuit Composed of a Transcription Factor, IscR, and a Regulatory RNA, RyhB, Controls Fe—S Cluster Delivery.", MBIO Sep. 20, 2016, vol. 7, No. 5, Sep. 20, 2016.
European Search Report for European Application No. EP18747944.9, dated Nov. 6, 2020, 13 pages.
European Search Report for European Application No. EP18744050.8, dated Oct. 28, 2020, 13 pages.

\* cited by examiner

FIGURE 7B

| Library | Positions and Mutations | | | | | | | | | # of Constructs |
|---|---|---|---|---|---|---|---|---|---|---|
| lib1 | V30<br>V,I | S32<br>S,T | T34<br>T,C | N35<br>N,T | R37<br>D,K,L,R,P,E,N | | | | | 112 |
| lib2 | V59<br>V,I | V61<br>V,C | S62<br>A,S,T | V63<br>V,C | L83<br>L,I,V | V84<br>V,I | | | | 144 |
| lib3 | C104<br>C,K,G,A | L105<br>L,I,V | S301<br>S,A | I302<br>I,V | I303<br>I,M,L | V306<br>V,A | | | | 288 |
| lib4 | P131<br>P,S,A | I132<br>I,M | I134<br>I,V | A138<br>A,S,G | K143<br>K,R | | | | | 72 |
| lib5 | F176<br>F,I,L,Y | K177<br>K,V,I | V178<br>V,I | V180<br>V,L,I,M | A182<br>A,S | | | | | 192 |
| lib6 | L205<br>L,V,I | I207<br>I,V | A210<br>A,S | G212<br>G,T | A213<br>A,L,V,I | | | | | 96 |
| lib7 | L236<br>L,I,M | V238<br>V,I | A241<br>A,S,T | A242<br>A,G | D243<br>D,E | | | | | 72 |
| lib8 | R259<br>R,G | S262<br>S,T | R263<br>R,G,E | I265<br>I,S | N266<br>N,E,K,D | | | | | 360 |
| lib9 | F267<br>I,F,L,V | I268<br>I,V | A269<br>A,S | T272<br>T,S | S274<br>S,G,A | Q276<br>Q,T | E277<br>E,Q,G,N,R | F278<br>F,I | D289<br>D,N | 3840 |

METABOLIC ENGINEERING FOR MICROBIAL PRODUCTION OF TERPENOID PRODUCTS

CROSS-REFERENCE TO RELATED APPLICATIONS

This application claims the benefit of and priority to U.S. Provisional Patent Application No. 62/454,121, filed Feb. 3, 2017, the content of which is hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on Apr. 29, 2020, is named MAN-008C1_Sequence_Listing.txt and is 20,480 bytes in size.

BACKGROUND

The food and beverage industries as well as other industries such as the perfume, cosmetic and health care industries routinely use terpenes and/or terpenoid products, including for use as flavors and fragrances. However, factors such as: (i) the availability and high price of the plant raw material; (ii) the relatively low terpene content in plant; and (iii) the tedious and inefficient extraction processes to produce sufficient quantities of terpene products on an industrial scale all have stimulated research on the biosynthesis of terpenes using plant-independent systems. Consequently, effort has been expended in developing technologies to engineer microorganisms for converting renewable resources such as glucose into terpenoid products. By comparison with traditional methods, microorganisms have the advantage of fast growth without the need for land to sustain development.

There are two major biosynthetic routes for the essential isoprenoid precursors isopentenyl diphosphate (IPP) and dimethylallyl diphosphate (DMAPP), the mevalonate (MVA) pathway and the methylerythritol phosphate (MEP) pathway. The MVA pathway is found in most eukaryotes, archaea and a few eubacteria. The MEP pathway is found in eubacteria, the chloroplasts of plants, cyanobacteria, algae and apicomplexan parasites. *E. coli* and other Gram-negative bacteria utilize the MEP to synthesize IPP and DMAPP metabolic precursors. While the MEP pathway provides a theoretically better stoichiometric yield over the MVA pathway, the MEP pathway in *E. coli* and in other bacteria has a variety of intrinsic regulation mechanisms that control and/or limit carbon flux through the pathway. See, Zhao et al., *Methylerythritol Phosphate Pathway of Isoprenoid Biosynthesis*, Annu Rev. Biochem. 2013; 82:497-530; Ajikumar P K, et al., *Isoprenoid pathway optimization for Taxol precursor overproduction in Escherichia coli.* Science 2010; 330-70-74.

Microbial strains and methods for improving carbon flux through the MEP pathway are needed for industrial-scale production of terpenes and terpenoids in bacterial systems.

SUMMARY OF THE INVENTION

In various aspects, the invention relates to methods and bacterial strains (such as *E. coli*) for making terpene and terpenoid products. In certain aspects, the invention provides bacterial strains with improved carbon flux through the MEP pathway, to thereby increase terpene and/or terpenoid product yield by fermentation with carbon sources such as glucose. For example, in some embodiments the method comprises providing a bacterial strain that produces isopentenyl diphosphate (IPP) and dimethylallyl diphosphate (DMAPP) through the MEP pathway, and converts the IPP and DMAPP to a terpene or terpenoid product through a downstream synthesis pathway. The bacterial strain, when cultured with a carbon source such as glucose, metabolizes greater than 1% of the carbon entering glycolysis through the MEP pathway, and in various embodiments metabolizes greater than 15% of the carbon entering glycolysis through the MEP pathway (greater than 15% "MEP carbon").

In various embodiments, the invention involves "tuning" down expression or activity of one or more competing enzymes or pathways in the bacterial production strain, such as the ubiquinone synthesis pathway, without substantial or measurable impact on strain growth or viability. In some embodiments, the expression or activity of the IspB enzyme is decreased, optionally by modification to the ribosomal binding sequence (RBS), promoter, or amino acid sequence, or replacement with an IspB ortholog.

Alternatively, or in addition, the invention involves increasing the availability or activity of Fe—S cluster proteins, so as to support higher activity of the Fe—S enzymes IspG and/or IspH, optionally by altering expression of the isc operon, and/or by deletion of the ryhB small RNA.

Alternatively, or in addition, in some embodiments the invention involves tuning the activity of IspG and/or IspH by overexpression and/or by selection of beneficial mutants or ortholog(s). Such mutants or orthologs can increase MEP carbon by pulling carbon further down the MEP pathway. Alternatively, or in addition, MEP enzyme complementation as evaluated by metabolomics can identify MEP enzyme complementation that results in high MEP carbon, with carbon pulled further down the pathway to the MEcPP intermediate.

In certain embodiments, the bacterial cell produces one or more terpenoid compounds, such as monoterpenoids, sesquiterpenoids, and diterpenoids, among others. Such terpenoid compounds find use in perfumery (e.g., patchoulol), in the flavor industry (e.g., nootkatone), as sweeteners (e.g., steviol glycosides), or therapeutic agents (e.g., taxol).

The host cell will generally contain a recombinant downstream pathway that produces the terpene or terpenoid from IPP and DMAPP precursors.

The recovered terpene or terpenoid may be incorporated into a product (e.g., a consumer or industrial product). For example, the product may be a flavor product, a fragrance product, a sweetener, a cosmetic, a cleaning product, a detergent or soap, or a pest control product. The higher yields produced in embodiments of the invention can provide significant cost advantages as well as sustainability and quality control of the terpene or terpenoid ingredient.

In other aspects, the invention provides bacterial cells, such as *E. coli*, having one or more genetic modifications that increase MEP carbon, as described in detail herein.

Other aspects and embodiments of the invention will be apparent from the following detailed description of the invention.

DESCRIPTION OF THE FIGURES

FIG. 3 shows experiments where a shift of 40% carbon from DOX to ME is observed in going from Strain G2 to G4.

FIGS. 7A-B illustrate IspG enzyme engineering. Mutation libraries of wild-type *E. coli* IspG gene were designed based on predicted changes to a structural model (FIG. 7A). Libraries were designed for improved kinetics, protein stability, or strain robustness. Specific variants were introduced at discrete locations in the sequence in each separate library (FIG. 7B). Nine total combinatorial libraries were designed using sequence alignments to ~1000 diverse ispG orthologs.

DETAILED DESCRIPTION OF THE INVENTION

In various aspects, the invention relates to bacterial strains and methods for making terpene and terpenoid products. In certain aspects, the invention provides bacterial strains with improved carbon flux through the MEP pathway, to thereby increase terpene and/or terpenoid product yield by fermentation with carbon sources such as glucose. For example, in some embodiments the method comprises providing a bacterial strain that produces isopentenyl diphosphate (IPP) and dimethylallyl diphosphate (DMAPP) through the MEP pathway, and converts the IPP and DMAPP to a terpene or terpenoid product through a downstream synthesis pathway. The bacterial strain, when cultured with a carbon source such as glucose, metabolizes greater than 1% of the carbon entering glycolysis through the MEP pathway (greater than 1% "MEP carbon"). In some embodiments, at least about 5%, at least about 10%, at least about 15%, at least about 17%, or at least about 20% of carbon entering glycolysis becomes MEP carbon. In still other embodiments, at least about 22% or at least about 25% or at least about 27% of carbon entering glycolysis becomes MEP carbon. With glucose as carbon source, the theoretical maximum for carbon entering the MEP pathway is about 30% in *E. coli*. In some embodiments, the strain substantially meets this theoretical maximum yield of MEP carbon, meaning that the strain provides at least about 80% of the maximum theoretical yield. Prior yields of MEP carbon reported in the literature are less than 1%. See, Zhou K, Zou R, Stephanopoulos G, Too H-P (2012) *Metabolite Profiling Identified Methylerythritol Cyclodiphosphate Efflux as a Limiting Step in Microbial Isoprenoid Production*. PLoS ONE 7(11): e47513. doi:10.1371/journal.pone.0047513.

In various embodiments, the microbial strain is a bacteria selected from *Escherichia* spp., *Bacillus* spp., *Rhodobacter* spp., *Zymomonas* spp., or *Pseudomonas* spp. In some embodiments, the bacterial species is selected from *Escherichia coli, Bacillus subtilis, Rhodobacter capsulatus, Rhodobacter sphaeroides, Zymomonas mobilis*, or *Pseudomonas putida*. In some embodiments, the bacterial strain is *E. coli*.

Figure 1:
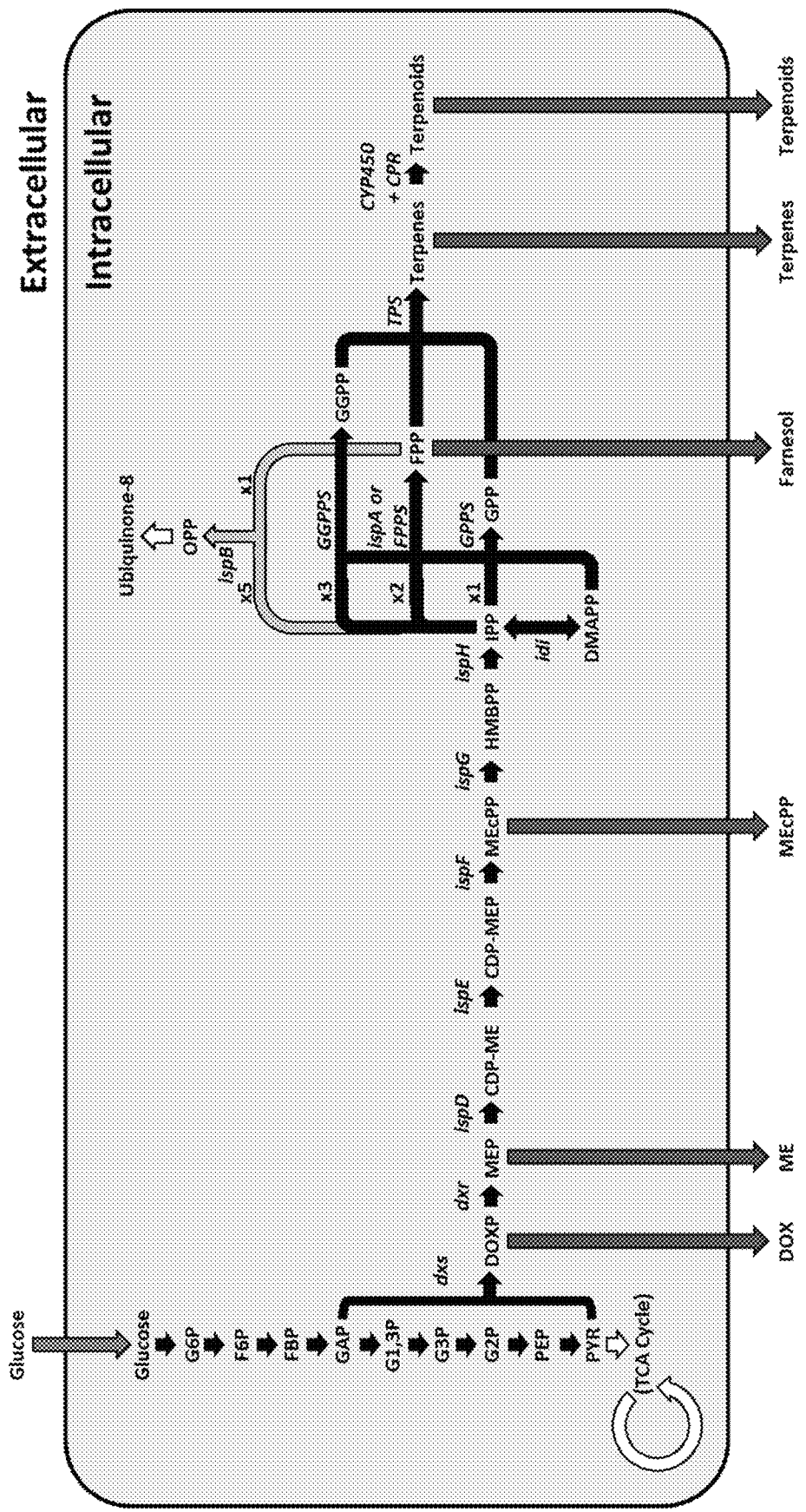
FIG. 1 is a schematic for terpenoid production through the MEP pathway. A bacterial cell is represented, taking in glucose as a carbon source. Glucose is converted to biomass through the TCA cycle or funneled through the MEP pathway to the desired terpenoid products. Glucose comes into the cell and is converted to pyruvate (PYR) with glyceraldehyde-3-phosphate as an intermediate (GAP). PYR and GAP are combined to make DOXP, which is converted to MEP and commits the pathway to FPP (going through MEcPP). DOX and ME are dephosphorylated products of DOXP and MEP, respectively. DOX, ME, and MEcPP are found outside the cell. The more flux that is forced into the MEP pathway, the more these products are found extracellularly. These side products can be used as markers of bottlenecks in the MEP pathway, and to identify targets for engineering. Black arrows show enzyme-mediated biochemical reactions towards terpenoids, light grey arrows show a competing side product, dark grey arrows show transport of a product outside of the cell, and white arrows show condensed pathways for simplicity.

The host bacterial cell expresses an MEP pathway producing isopentenyl diphosphate (IPP) and dimethylallyl diphosphate (DMAPP). Glucose comes into the cell and is converted to pyruvate (PYR) with glyceraldehyde-3-phosphate as an intermediate (G3P or GAP). G3P and PYR are combined to make 1-deoxy-D-xylulose-5-phosphate (DOXP), which is converted to 2-C-methyl-D-erythritol 4-phosphate (MEP) and commits the pathway to IPP and DMAPP. DOX, ME, and MEcPP are found outside the cell. The more flux into the MEP pathway, the more these products are found extracellularly. See FIG. 1.

The MEP (2-C-methyl-D-erythritol 4-phosphate) pathway is also called the MEP/DOXP (2-C-methyl-D-erythritol 4-phosphate/1-deoxy-D-xylulose 5-phosphate) pathway or the non-mevalonate pathway or the mevalonic acid-independent pathway. The pathway typically involves action of the following enzymes: 1-deoxy-D-xylulose-5-phosphate synthase (Dxs), 1-deoxy-D-xylulose-5-phosphate reductoisomerase (Dxr, or IspC), 4-diphosphocytidyl-2-C-methyl-D-erythritol synthase (IspD), 4-diphosphocytidyl-2-C-methyl-D-erythritol kinase (IspE), 2C-methyl-D-erythritol 2,4-cyclodiphosphate synthase (IspF), 1-hydroxy-2-methyl-2-(E)-butenyl 4-diphosphate synthase (IspG), 1-hydroxy-2-methyl-2-(E)-butenyl 4-diphosphate reductase (IspH) and isopentenyl diphosphate isomerase (Idi). The MEP pathway, and the genes and enzymes that make up the MEP pathway, are described in U.S. Pat. No. 8,512,988, which is hereby incorporated by reference in its entirety. Thus, genes that make up the MEP pathway include dxs, dxr (or ispC), ispD, ispE, ispF, ispG, ispH, idi, and ispA.

IPP and DMAPP (the products of the MEP pathway) are the precursors of terpenes and terpenoids, including monoterpenoids, sesquiterpenoids, diterpenoids, and triterpenoids, which have particular utility in the flavor, fragrance, cosmetics, and food sectors. Synthesis of terpenes and terpenoids proceeds via conversion of IPP and DMAPP precursors to geranyl diphosphate (GPP), farnesyl diphosphate (FPP), or geranylgeranyl diphosphate (GGPP), through the action of a prenyl transferase enzyme (e.g., GPPS, FPPS, or GGPPS). Such enzymes are known, and are described for example in U.S. Pat. No. 8,927,241, WO 2016/073740, and WO 2016/029153, which are hereby incorporated by reference in their entireties.

As used herein, the term "MEP carbon" refers to the total carbon present as an input, intermediate, metabolite, or product of the MEP pathway. Metabolites include derivatives such as breakdown products, and products of phosphorylation and dephosphorylation. MEP carbon includes products and intermediates of downstream pathways including terpenoid synthesis pathways. For purposes of this disclosure, MEP carbon includes the following inputs, intermediates, and metabolites of the MEP pathway: D-glyceraldehyde 3-phosphate, pyruvate, 1-deoxy-D-xylulose-5-phosphate, 1-deoxy-D-xylulose, 2-C-methyl-D-erythritol-5-phosphate, 2-C-methyl-D-erythritol, 4-diphosphocytidyl-2-C-methyl-D-erythritol, 2-phospho-4-diphosphocytidyl-2-C-methyl-D-erythritol, 2C-methyl-D-erythritol 2,4-cyclodiphosphate, 1-hydroxy-2-methyl-2-(E)-butenyl 4-diphosphate, isopentenyl diphosphate, and dimethylallyl diphosphate. MEP carbon further includes intermediates and key metabolites in the downstream terpenoid synthesis pathway expressed by the cell. While the identity will vary based upon pathway and enzymes employed, such products include: geranyl diphosphate (GPP), farnesyl diphosphate (FPP), geranylgeranyl diphosphate (GGPP), or geranylfarnesyl diphosphate (FGPP); their monophosphorylated versions geranyl phosphate, farnesyl phosphate, geranylgeranyl phosphate, or geranylfarnesyl phosphate; their alcohols geraniol, farnesol, geranylgeraniol, or geranylfarnesol; as well as downstream terpene and terpenoid products. MEP carbon further includes compounds derived from FPP or pathways that use FPP, including squalene, undecaprenyl diphosphate (UPP), undecaprenyl phosphate, octaprenyl diphosphate (OPP), 4-hydroxybenzoate, 3-octaprenyl-4-hydroxybenzoate, 2-octaprenylphenol, 3-octaprenylbenzene-1,2-diol, 2-methoxy-6-octaprenyl-2-methoxy-1, 4-benzoquinol, 6-methoxy-3-methyloctaprenyl-1,4-benzoquinol, 3-demethyluibquinol-8, ubiquinol-8, ubiquinone, 2-carboxy-1,4-naphthoquinol, demethylmenaquinol-8, menaquinol-8, and menaquinone. MEP carbon further includes isoprenol, prenol, isopentenyl phosphate, and dimethylallyl phosphate metabolites. MEP carbon further includes prenylated metabolites and proteins, including prenylated indole. MEP carbon (the intermediates and metabolites above) can be quantified by mass spectrometry (MS), such as tandem mass spectrometry (MS/MS) via triple quadrupole (QQQ) mass detector. An exemplary system is Agilent 6460 QQQ; alternatively with quantitative time-of-flight (QTOF), time-of-flight (TOF), or ion trap mass detectors.

Exemplary terpene or terpenoid products that may be produced in accordance with the invention are described in U.S. Pat. No. 8,927,241, which is hereby incorporated by reference, and include: alpha-guaiene, alpha-sinensal, amorphadiene, artemisinic acid, beta-bisabolene, beta-Thujone, Camphor, Carveol, Carvone, Cineole, Citral, Citronellal, Cubebol, Geraniol, Limonene, Menthol, Menthone, Myrcene, Nootkatone, Nootkatol, Patchouli, Piperitone, Rotundone, Rose oxide, Sabinene, Steviol, Steviol glycoside (including Rebaudioside D or Rebaudioside M), Taxadiene, Thymol, and Valencene. Enzymes for recombinantly constructing the pathways in *E. coli* are described in U.S. Pat. No. 8,927,241, WO 2016/073740, and WO 2016/029153, which are hereby incorporated by reference.

In some embodiments, the microbial strain has at least one additional copy of one or more of dxs, ispD, ispF, and/or idi genes, which can be rate limiting, and which can be expressed from an operon or module, either on a plasmid or integrated into the bacterial chromosome. In some embodiments, the bacterial strain has at least one additional copy of dxs and idi expressed as an operon/module; or dxs, ispD, ispF, and idi expressed as an operon or module. In these embodiments, the strain provides increased flux through the MEP pathway as compared to wild type. Complementation of the MEP pathway as described below, can be in addition to dxs, ispD, ispF, and/or idi overexpression.

In various embodiments, the invention involves "tuning" down expression or activity of one or more competing enzymes or pathways, such as the ubiquinone synthesis pathway or the IspB enzyme, which competes for FPP. Alternatively, or in addition, the invention involves increasing the availability or activity of Fe—S cluster proteins, so as to support higher activity of IspG and IspH, which are Fe—S enzymes. Alternatively, or in addition, in some embodiments the invention involves overexpression or tuning the expression or activity IspG and/or IspH, for example by selection of beneficial mutants or orthologs that have the effect of increasing MEP carbon by pulling carbon further down the pathway. Alternatively, or in addition, further MEP enzyme complementation as evaluated by metabolomics can identify MEP enzyme complementation that results in high MEP carbon. These and other embodiments are described in detail below.

In various embodiments, the microbial strain provides substantial increases in MEP carbon, without substantial impact on strain growth and viability with glucose as a carbon source, for example, as determined by optical density (O.D.) in culture, peak O.D., and/or growth rate. For example, despite modifications to one or more essential genes or pathways as described herein, the microbial strain does not exhibit a drop in peak O.D. of more than about 20%, or in some embodiments, does not exhibit a drop in peak O.D. of more than about 15%, or more than about 10%, or more than about 5%. In some embodiments, the strain does not exhibit a measurable impact on strain growth or viability, as determined for example by measuring growth rate or peak O.D.

In some embodiments, the ubiquinone biosynthesis pathway is downregulated, for example, by reducing the expression or activity of IspB, which uses IPP and FPP substrate. The ispB gene encodes an octaprenyl diphosphate synthase that controls the synthesis of ubiquinone and thus directly competes with FPP synthase for IPP and DMAPP precursors. IspB is an essential gene in *E. coli*. See, Kainou T, et al., *Dimer formation of octaprenyl-diphosphate Synthase (IspB) is essential for chain length determination of ubiquinone*, J. Biol. Chem. 276(11):7867-7883 (2001). However, decreasing the amount of IspB enzyme in the cell by modifying the ispB RBS sequence and turning down translation of the mRNA can shift carbon flux towards the terpenoid recombinant pathway, without substantial or measurable impact on the growth and viability of the strain. In some embodiments, IspB activity or expression is reduced to about 80% or less of the parent strain, or about 70% or less of the parent strain, or 50% or less of the parent strain, or 40% or less of the parent strain, or 25% or less of the parent strain.

The Shine-Dalgarno (SD) sequence is the ribosomal binding site in bacteria and is generally located around 8 bases upstream of the start codon AUG. The RNA sequence helps recruit the ribosome to the messenger RNA (mRNA) to initiate protein synthesis by aligning the ribosome with the start codon. In some embodiments, the six-base SD sequence in the ispB gene is changed to CGTGCT or CGTGCC, or a modification thereof having one or two nucleotide changes from CGTGCT or CGTGCC. In such embodiments, the IspB translation is tuned down, allowing for increased carbon flux to terpenoid biosynthesis, without substantial or measurable impact on *E. coli* growth and viability.

In some embodiments, the expression or activity of IspB is modified by altering expression of the ispB gene, that is, by modifying the promoter region to decrease transcription, or by enhancing the rate of degradation of the ispB RNA or encoded protein. In some embodiments, the activity of the ispB enzyme is decreased by mutation of the ispB amino acid sequence or selection of an ispB ortholog with decreased activity in the bacterial strain. The wild type IspB amino acid sequence from *E. coli* is provided herein as SEQ ID NO:3. In some embodiments, from 1 to about 10, or from 1 to about 5, amino acid substitutions, deletions, and/or insertions are made to the IspB amino acid sequence (SEQ ID NO:3) to decrease the activity of the protein, including one or more substitutions to the substrate binding site and/or active site. In some embodiments, the amino acid sequence (whether an ortholog or mutant sequence) has from about 50% to about 99% sequence identity with SEQ ID NO:3, or about 60% to about 99% sequence identity to SEQ ID NO:3, or from about 70% to about 99% sequence identity to SEQ ID NO:3, or from about 80% to about 99% sequence identity to SEQ ID NO:3, or from about 90% to about 99% sequence identity to SEQ ID NO:3, or from about 95% to about 99% sequence identity with the amino acid sequence of SEQ ID NO:3. Such mutants and orthologs can be informed by Kainou T, et al., *Dimer formation of octaprenyl-diphosphate Synthase (IspB) is essential for chain length determination of ubiquinone*, J. Biol. Chem. 276(11):7867-7883 (2001); or Han, et al., *Crystal structures of ligand-bound octaprenyl pyrophosphate synthase from Escherichia coli reveal the catalytic and chain-length determining mechanisms Proteins* 2015 January; 83 (1):37-45.

In some embodiments, the bacterial strain supports enhanced biology of Fe—S enzymes, such as IspG and/or IspH, to potentially improve the amount of MEP carbon in the strain. The IspG and IspH enzymes in the MEP pathway are iron-sulphur cluster enzymes, meaning that they need a special arrangement of Fe—S ions in their active sites to function and do their chemistry. These Fe—S clusters are critical to life, and are incredibly sensitive to oxygen and oxygenation, which inactivates them. Under either anaerobic or aerobic growth conditions, iscR represses transcription of the operon iscRSUA, which encodes genes for the Fe—S cluster biogenesis pathways. The repression of the isc operon by iscR responds to the demand for the Fe—S cluster in the medium, because iscR has to be bound to an Fe—S group to be able to repress the transcription of the isc operon. Under anaerobiosis, the demand for the Fe—S group is lower than under aerobiosis, and therefore the repression of the operon is stronger than under aerobiosis. iscR recognizes and binds two DNA-binding sites that overlap the promoter sequence to repress transcription of the iscRSUA operon. When the protein is bound to these sites, the RNA polymerase is most likely not able to bind to the promoter region to start transcription.

In some embodiments the isc operon is expressed under conditions used for terpene or terpenoid production using either a strong, intermediate, or weak bacterial promoter. The strength of the promoter can be varied and tuned to improve terpenoid product. The promoter can be constitutive or inducible. In some embodiments, the promoter is a strong constitutive promoter.

Upon deleting the promoter and first gene of the isc operon (namely iscR) and replacing it with a constitutive or inducible promoter to drive expression of the genes remaining in the operon, improvements in iron-sulfur cluster enzyme performance are obtained. Thus, in some embodiments, the bacterial strain (e.g., *E. coli*) contains an iscR deletion, with inducible or constitutive overexpression of iscSUA. Inducible and constitutive promoters for *E. coli* are known, and can be selected by one of skill in the art to tune expression of the operon. In various embodiments, the iscR gene is fully or partly deleted, or is inactivated by one or more mutations to the RBS or start codon. In some embodiments, the iscR gene is inactivated by amino acid mutation. In the various embodiments, the modifications to Fe—S enzyme regulation increase MEP carbon without substantial or measurable impact on growth or viability of the strain, including under the aerobic or microaerobic conditions often used for terpenoid production in *E. coli*. The isc operon is further reviewed in Santos J A, *What a difference a cluster makes: The multifaceted roles of IscR in gene regulation and DNA recognition, Biochim. Biophys. Acta* 1854 (9):1102-12 (2015).

In some embodiments, the *E. coli* contains a ryhB deletion or inactivation. RyhB is a small RNA which acts to reduce iron consumption under low-iron conditions by downregulating expression of iron-containing proteins, including enzymes of the TCA cycle and the aerobic respiratory chain. In addition, ryhB promotes synthesis of the siderophore enterobactin. RyhB is a small RNA of approximately 90 nt in length. RyhB promotes cleavage of the polycistronic iscRSUA mRNA between the iscR and iscS open reading frames. The IscR-encoding 5' fragment remains stable, while the iscSUA 3' fragment appears to be degraded. See Mandin et al., (2016) *A regulatory circuit composed of a transcription factor, IscR, and a regulatory RNA, RyhB, controls Fe—S cluster delivery, mBio* 7 (5):e00966-16. In various embodiments, deletion or inactivation (e.g., by nucleotide mutation) of ryhB increases MEP carbon, without substantial or measurable impact on strain growth or viability, including under aerobic, microaerobic, or anaerobic conditions used for screening of strains or production of terpenoids.

Figure 13:
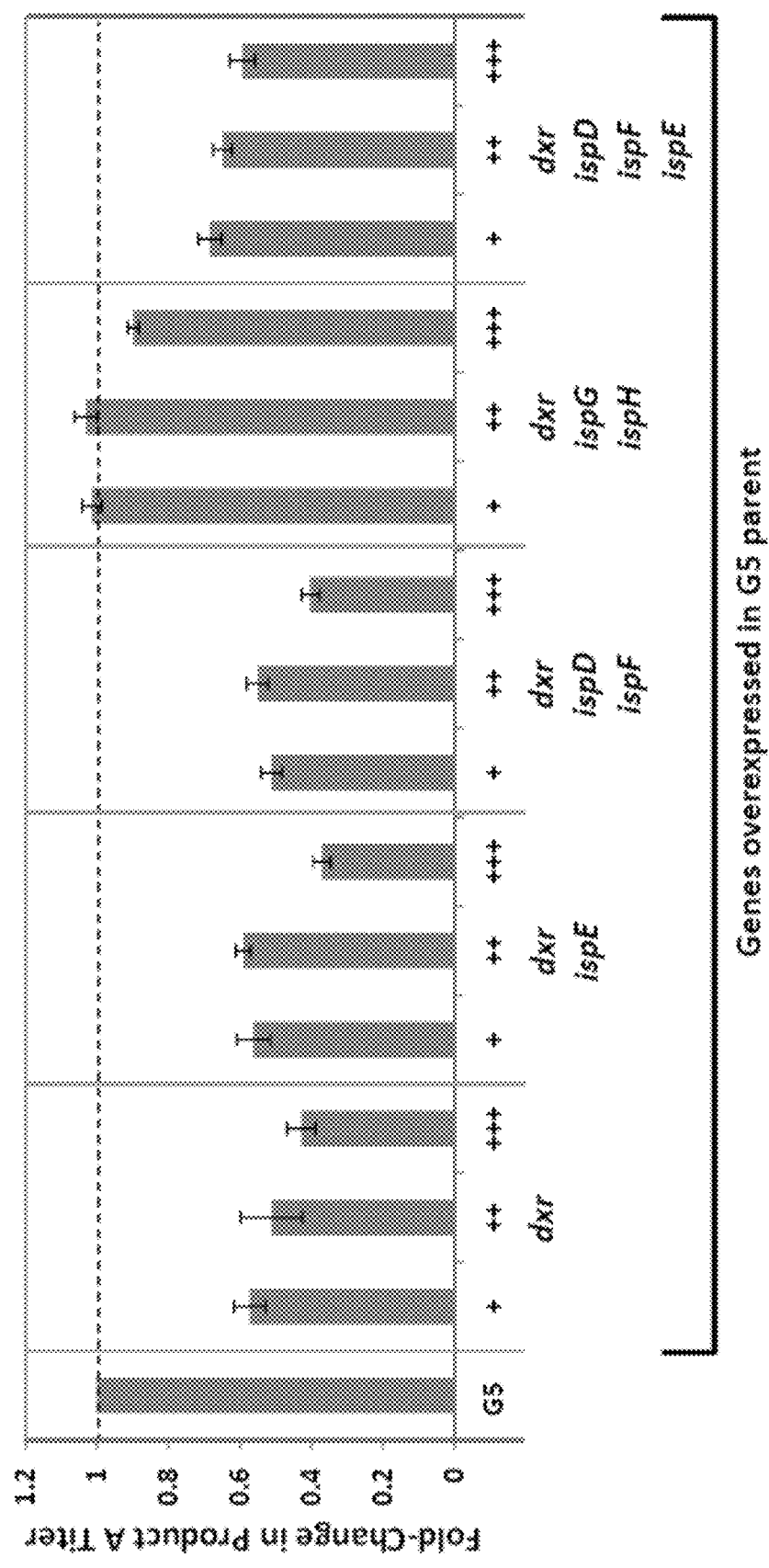
FIG. 13 shows that overexpression of MEP genes causes drop in product titer. Increasing the expression level of MEP genes over the G5 parent levels results in ~50% less terpenoid Product A produced, with stronger expression (+++) exacerbating the decrease over weaker expression (+). In contrast, the addition of ispG and ispH genes to an operon expressing dxr enables recovery of product titer to parental levels, indicating that careful balancing of gene expression in this pathway will enable high terpenoid product titers.

In some embodiments, MEP enzyme expression or activity, is altered or balanced to move carbon further down the pathway, for example, by complementation with additional enzyme copies, whether on plasmids or integrated into the genome. As shown in FIG. 13, overexpression of MEP genes can cause a drop in product titer. For example, increasing the expression level of MEP genes over the G5 parent levels results in ~50% less terpenoid Product A produced, with stronger expression (+++) exacerbating the decrease over weaker expression (+). In contrast, the addition of ispG and ispH genes to an operon expressing dxr enables recovery of product titer to parental levels, indicating that careful balancing of gene expression in this pathway will enable high terpenoid product titers.

While Product A titer dropped or stayed the same with MEP complementation, the intermediate MEP pathway metabolites increased significantly more in concentration. The majority of MEP intermediates are observed outside the cell, with DOX, ME, and MEcPP representing the majority; the major intracellular product is CDP-ME, with increasing accumulation observed in complemented strains. While dxr overexpression caused the Product A titer to drop by two-fold, the amount of carbon entering the MEP pathway and accumulating as intermediates went up six-fold, that is, more carbon is entering the MEP pathway, but less of it is getting out. Moreover, while the G5 parent accumulated mostly DOX (and some MEcPP), the increase in dxr (which converts DOXP to MEP) shifts the carbon down the pathway, resulting in more carbon pooling extracellularly as ME and MEcPP. Increasing ispE expression on top of dxr further increases the amount of carbon in the MEP pathway to almost ten-fold over the G5 parent, and shifted almost all of that carbon downstream to MEcPP. Interestingly, overexpressing ispG and ispH in addition to dxr gives a very similar intermediate profile to overexpressing dxr only, though the product titer is doubled in the former instance.

In some embodiments, the bacterial strain contains an overexpression of dxr or homolog or ortholog thereof and ispG and/or ispH, optionally with one or more of an overexpression of ispD, ispE, and ispF. The genes can be overexpressed individually or in an operon. The additional copies can be expressed from a plasmid or integrated into the genome. Overexpression of dxr pushes DOXP to ME and MEcPP and pushes the bottleneck downstream. See FIG. 1. In some embodiments, dxr and ispE (or homologs, orthologs, or derivatives thereof) are overexpressed, which pushes DOXP to primarily MEcPP. See FIG. 14. Upon shifting the bottleneck to MEcPP, a tripling of MEP pathway potential can be observed (FIG. 15).

The wild type Dxr amino acid sequence from *E. coli* is provided as SEQ ID NO:4. In some embodiments, wild-type dxr activity is complemented with one or more additional gene copies, which may encode the wild-type enzyme, or may encode a non-native or modified enzyme with one or more amino acid modifications (e.g., from one to ten modifications independently selected from substitutions, insertions, and deletions) to increase enzyme activity or stability. In some embodiments, the bacterial strain is complemented with a dxr ortholog having higher activity than the *E. coli* enzyme.

In some embodiments, the bacterial strain expresses *Brucella abortus* DRL enzyme (SEQ ID NO: 8), which is a Dxr-like enzyme having low sequence homology to *E. coli* Dxr. Pérez-Gil, J., et al., 2012. *Crystal structure of brucella abortus deoxyxylulose-5-phosphate reductoisomerase-like (DRL) enzyme involved in isoprenoid biosynthesis. Journal of Biological Chemistry*, 287(19), pp. 15803-15809. In some embodiments, the DRL enzyme has one or more amino acid modifications (e.g., from one to ten modifications independently selected from substitutions, insertions, and deletions) that improve the properties of the enzyme for activity and/or expression in the bacterial host cell.

For example, in various embodiments the bacterial strain overexpresses or is complemented with a Dxr enzyme having 50% or more sequence identity with SEQ ID NO: 4 or 8, or at least about 60% sequence identity, or at least about 70% sequence identity, or at least about 80% sequence identity, or at least about 90% sequence identity, or at least about 95% sequence identity, or at least 97% sequence identity with the amino acid sequence of SEQ ID NO: 4 or 8. In some embodiments, the Dxr enzyme comprises from 1 to about 10, or from 1 to about 5, amino acid substitutions, deletions, and/or insertions with respect to the Dxr or DRL amino acid sequence (e.g., SEQ ID NO: 4 or 8) to alter the activity of the protein, including substitutions to one or more of the substrate binding site and/or active site. Such mutants can be informed by enzyme structures available in the art, including Yajima S, et al., *Structure of 1-deoxy-D-xylulose 5-phosphate reductoisomerase in a quaternary complex with a magnesium ion, NADPH and the antimalarial drug fosmidomycin, Acta Cryst.* F63, 466-470 (2007) and Perez-Gil, et al., *Crystal structure of brucella abortus deoxyxylulose-5-phosphate reductoisomerase-like (DRL) enzyme involved in isoprenoid biosynthesis, Journal of Biological Chemistry,* 287 (19): 15803-15809 (2012).

In some embodiments, wild-type IspE activity is complemented with one or more additional gene copies, which may encode the wild-type enzyme, or may encode a modified enzyme with one or more amino acid modifications (e.g., from one to ten modifications independently selected from substitutions, insertions, and deletions) to increase enzyme activity or stability. In some embodiments, the bacterial strain is complemented with an IspE ortholog having higher activity than the *E. coli* or native bacterial enzyme. The *E. coli* IspE amino acid sequence is provided as SEQ ID NO: 7. In some embodiments, the bacterial strain expresses at least one additional gene copy of ispE or a derivative, homolog, or ortholog thereof. In some embodiments, the additional IspE enzyme is *E. coli* IspE or comprises one or more amino acid modifications (e.g., from one to ten modifications independently selected from substitutions, insertions, and deletions) which may provide for increased activity and/or stability of the enzyme.

For example, in various embodiments the bacterial strain overexpresses or is complemented with an IspE enzyme having 50% or more sequence identity with SEQ ID NO: 7, or at least about 60% sequence identity, or at least about 70% sequence identity, or at least about 80% sequence identity, or at least about 90% sequence identity, or at least about 95% sequence identity, or at least 97% sequence identity with the amino acid sequence of SEQ ID NO: 7.

In some embodiments, the strain includes complementation with IspG and/or IspH. In some embodiments, the additional gene may be identical or substantially identical to the native gene, or may be modified to increase activity, or may be an IspG or IspH ortholog having higher activity than the native bacterial (e.g., *E. coli*) enzyme. For example, with respect to IspG, the amino acid sequence may have 50% or more sequence identity with SEQ ID NO:5, or at least about 60% sequence identity, or at least about 70% sequence identity, or at least about 80% sequence identity, or at least about 90% sequence identity, or at least about 95% sequence identity, or at least about 97% sequence identity with the amino acid sequence of SEQ ID NO:5. In some embodiments, from 1 to about 10, or from 1 to about 5, amino acid substitutions, deletions, and/or insertions are made to the IspG amino acid sequence (SEQ ID NO:5) to alter the activity of the protein, including substitutions to one or more of the substrate binding site or active site. Modifications to *E. coli* or other IspG can be informed by construction of a homology model. For example, a suitable homolog for construction of an *E. coli* IspG homology model is disclosed in: Lee M, et al. *Biosynthesis of isoprenoids: crystal structure of the [4Fe-4S] cluster protein IspG. J Mol Biol.* 2010 Dec. 10; 404(4):600-10.

In some embodiments, the IspG enzyme contains one or more mutations at positions selected from V30, S32, T34, N35, R37, V59, V61, S62, V63, L83, V84, C104, L105, P131, I132, I134, A138, K143, F176, K177, V178, V180, A182, L205, I207, A210, G212, A213, L236, V238, A241, A242, D243, R259, S262, R263, I265, N266, F267, I268, A269, T272, S274, Q276, E277, F278, D289, S301, I302, I303, V306. In some embodiments, modifications are made at a plurality of positions selected from: (1) V30, S32, T34, N35, R37; or (2) V59, V61, S62, V63, L83, V84; or (3) C104, L105, S301, I302, I303, V306; or (4) P131, I132, I134, A138, K143; or (5) F176, K177, V178, V180, A182; or (6) L205, I207, A210, G212, A213; or (7) L236, V238, A241, A242, D243; or (8) R259, S262, R263, I265, N266; or (9) F267, I268, A269, T272, S274, Q276, E277, F278, D289.

In some embodiments, the IspG enzyme has one, two, three or all of the following mutations: L205V, A210S, G212T, and A213I.

Further, with respect to IspH, the amino acid sequence may have 50% or more sequence identity with SEQ ID NO:6, or at least about 60% sequence identity, or at least about 70% sequence identity, or at least about 80% sequence identity, or at least about 90% sequence identity, or at least about 95% sequence identity, or at least 97% sequence identity with the amino acid sequence of SEQ ID NO:6. In some embodiments, from 1 to about 10, or from 1 to about 5, amino acid substitutions, deletions, and/or insertions are made to the IspH amino acid sequence (SEQ ID NO:6) to alter the activity of the protein, including substitutions to one or more of the substrate binding site or active site. Modifications to the IspH enzyme can be informed by available IspH structures, including Grawert, T., et al. *Structure of active IspH enzyme from Escherichia coli provides mechanistic insights into substrate reduction* 2009 *Angew. Chem. Int. Ed. Engl.* 48: 5756-5759.

In these or other embodiments, pgi (glucose-6-phosphate isomerase) activity mutants (e.g., with reduced activity) are incorporated to potentially alter carbon flux, and may provide further improvements in product titer. In some embodiments, pgi is partially deleted or inactivated. In some embodiments, pgi contains from 1 to about 30 amino acid substitutions, insertions, and/or deletions (e.g., about 1 to 20, or about 1 to 10 amino acid substitutions, insertions, and/or deletions) to alter or tune the activity of the enzyme for product titer or MEP carbon.

The similarity of nucleotide and amino acid sequences, i.e. the percentage of sequence identity, can be determined via sequence alignments. Such alignments can be carried out with several art-known algorithms, such as with the mathematical algorithm of Karlin and Altschul (Karlin & Altschul (1993) *Proc. Natl. Acad. Sci. USA* 90: 5873-5877), with hmmalign (HMMER package, http://hmmer.wustl.edu/) or with the CLUSTAL algorithm (Thompson, J. D., Higgins, D. G. & Gibson, T. J. (1994) *Nucleic Acids Res.* 22, 4673-80). The grade of sequence identity (sequence matching) may be calculated using e.g. BLAST, BLAT or BlastZ (or BlastX). A similar algorithm is incorporated into the BLASTN and BLASTP programs of Altschul et al (1990) *J Mol. Biol.* 215: 403-410. BLAST polynucleotide searches can be performed with the BLASTN program, score=100, word length=12.

BLAST protein searches may be performed with the BLASTP program, score=50, word length=3. To obtain gapped alignments for comparative purposes, Gapped BLAST is utilized as described in Altschul et al (1997) *Nucleic Acids Res.* 25: 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:154-162) or Markov random fields.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups:

(1) hydrophobic: Met, Ala, Val, Leu, Ile;
(2) neutral hydrophilic: Cys, Ser, Thr; Asn, Gin;
(3) acidic: Asp, Glu;
(4) basic: His, Lys, Arg;
(5) residues that influence chain orientation: Gly, Pro; and
(6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt α-helices. Some preferred conservative substitutions within the above six groups are exchanges within the following sub-groups: (i) Ala, Val, Leu and Ile; (ii) Ser and Thr; (ii) Asn and Gin; (iv) Lys and Arg; and (v) Tyr and Phe.

As used herein, "non-conservative substitutions" are defined as exchanges of an amino acid by another amino acid listed in a different group of the six standard amino acid groups (1) to (6) shown above.

Modifications of enzymes as described herein can include conservative and/or non-conservative mutations.

In some embodiments "rational design" is involved in constructing specific mutations in enzymes. Rational design refers to incorporating knowledge of the enzyme, or related enzymes, such as its reaction thermodynamics and kinetics, its three dimensional structure, its active site(s), its substrate(s) and/or the interaction between the enzyme and substrate, into the design of the specific mutation. Based on a rational design approach, mutations can be created in an enzyme which can then be screened for increased production of a terpene or terpenoid relative to control levels. In some embodiments, mutations can be rationally designed based on homology modeling. As used herein, "homology modeling" refers to the process of constructing an atomic resolution model of one protein from its amino acid sequence and a three-dimensional structure of a related homologous protein.

In certain embodiments, the bacterial cell produces one or more terpene or terpenoid compounds. A terpenoid, also referred to as an isoprenoid, is an organic chemical derived from a five-carbon isoprene unit (C5). Several non-limiting examples of terpenoids, classified based on the number of isoprene units that they contain, include: hemiterpenoids (1 isoprene unit), monoterpenoids (2 isoprene units), sesquiterpenoids (3 isoprene units), diterpenoids (4 isoprene units), sesterterpenoids (5 isoprene units), triterpenoids (6 isoprene units), tetraterpenoids (8 isoprene units), and polyterpenoids with a larger number of isoprene units. In an embodiment, the bacterial host cell produces a terpenoid selected from a monoterpenoid, a sesquiterpenoid, diterpenoid, a sesterpenoid, or a triterpenoid. Terpenoids represent a diverse class of molecules that provide numerous commercial applications, including in the food and beverage industries as well as the perfume, cosmetic and health care industries. By way of example, terpenoid compounds find use in perfumery (e.g. patchoulol), in the flavor industry (e.g., nootkatone), as sweeteners (e.g., steviol), or therapeutic agents (e.g., taxol) and many are conventionally extracted from plants. Nevertheless, terpenoid molecules are found in ppm levels in nature, and therefore require massive harvesting to obtain sufficient amounts for commercial applications.

The host cell will generally contain a recombinant downstream pathway that produces the terpenoid from IPP and DMAPP precursors. Terpenes such as Monoterpenes (C10), Sesquiterpenes (C15), Diterpenes (C20), Sesterterpenes (C25), and Triterpenes (C30) are derived from the prenyl diphosphate substrates, geranyl diphosphate (GPP), farnesyl diphosphate (FPP), geranylgeranyl diphosphate (GGPP), geranylfarnesyl diphosphate (FGPP), and FPP, respectively, through the action of a very large group of enzymes called the terpene (terpenoid) synthases. These enzymes are often referred to as terpene cyclases since the product of the reactions are cyclized to various monoterpene, sesquiterpene, diterpene, sesterterpene and triterpene carbon skeleton products. Many of the resulting carbon skeletons undergo subsequence oxygenation by cytochrome P450 enzymes to give rise to large families of derivatives.

Exemplary cytochrome P450 enzymes that are operative on diterpene and sesquiterpene scaffolds are described in WO 2016/073740 and WO 2016/029153, which are hereby incorporated by reference. In addition, cytochrome P450 reductase proteins that find use in the bacterial strains described herein are described in WO 2016/029153 as well as WO 2016/073740.

The product of the invention in some embodiments is one or more oxygenated terpenoids. As used herein, the term "oxygenated terpenoid" refers to a terpene scaffold having one or more oxygenation events, producing a corresponding alcohol, aldehyde, carboxylic acid and/or ketone. In some embodiments, the bacterial cell produces at least one terpenoid selected from Abietadiene, Abietic Acid, alpha-Sinensal, artemisinic acid, beta-Thuj one, Camphor, Carveol, Carvone, Celastrol, Ceroplastol, Cineole, Citral, Citronellal, Cubebol, Cucurbitane, Forskolin, Gascardic Acid, Geraniol, Haslene, Levopimaric Acid, Limonene, Lupeol, Menthol, Menthone, Mogroside, Nootkatone, Nootkatol, Ophiobolin A, Patchouli, Piperitone, Rebaudioside D (RebD), Rebaudioside M (RebM), Sabinene, Steviol, Steviol glycoside, Taxadiene, Thymol, and Ursolic Acid.

In some embodiments, the terpenoid synthase enzyme is upgraded to enhance the kinetics, stability, product profile, and/or temperature tolerance of the enzyme, as disclosed, for example, in WO 2016/029153 and WO 2016/073740, which are hereby incorporated by reference.

In another embodiment, the bacterial cell produces valencene and/or nootkatone. In such an embodiment, the bacterial cell may express a biosynthetic pathway that further includes a farnesyl diphosphate synthase, a Valencene Synthase, and a Valencene Oxidase. Farnesyl diphosphate synthases (FPPS) produce farnesyl diphosphates from isopentenyl diphosphate (IPP) and dimethylallyl diphosphate (DMAPP). An exemplary farnesyl diphosphate synthase is ERG20 of *Saccharomyces cerevisiae* (NCBI accession P08524) and *E. coli* ispA. Valencene synthase produces sesquiterpene scaffolds and are described in, for example, US 2012/0107893, US 2012/0246767, and U.S. Pat. No. 7,273,735, which are hereby incorporated by reference in their entireties. Genes and host cells for the production of terpenoid product comprising valencene and/or nootkatone are described in WO 2016/029153, which is hereby incorporated by reference.

In an embodiment, the bacterial cell produces steviol or steviol glycoside (e.g., RebD or RebM). Steviol is produced from kaurene by the action of two P450 enzymes, kaurene oxidase (KO) and kaurenoic acid hydroxylase (KAH). After production of steviol, various steviol glycoside products may be produced through a series of glycosylation reactions, which can take place in vitro or in vivo. Pathways and enzymes for production of steviol and steviol glycosides are disclosed in US 2013/0171328, US 2012/0107893, WO 2012/075030, WO 2014/122328, which are hereby incorporated by reference in their entireties. WO 2016/073740 further discloses enzymes and bacterial host cells for production of RebM.

Other biosynthetic pathways for production of terpene or terpenoid compounds are disclosed in U.S. Pat. No. 8,927,241, which is hereby incorporated by reference in its entirety.

The bacterial host cell is cultured to produce the terpenoid product, and with enhanced MEP pathway flux. In some embodiments, carbon substrates such as C1, C2, C3, C4, C5, and/or C6 carbon substrates are employed for production of the terpene or terpenoid product. In exemplary embodiments, the carbon source is glucose, sucrose, fructose, xylose, and/or glycerol. Culture conditions are generally selected from aerobic, microaerobic, and anaerobic.

In various embodiments, the bacterial host cell may be cultured at a temperature between 22° C. and 37° C. While commercial biosynthesis in bacteria such as *E. coli* can be limited by the temperature at which overexpressed and/or foreign enzymes (e.g., enzymes derived from plants) are stable, recombinant enzymes (including the terpenoid synthase) may be engineered to allow for cultures to be maintained at higher temperatures, resulting in higher yields and higher overall productivity. In some embodiments, the culturing is conducted at about 22° C. or greater, about 23° C. or greater, about 24° C. or greater, about 25° C. or greater, about 26° C. or greater, about 27° C. or greater, about 28° C. or greater, about 29° C. or greater, about 30° C. or greater, about 31° C. or greater, about 32° C. or greater, about 33° C. or greater, about 34° C. or greater, about 35° C. or greater, about 36° C. or greater, or about 37° C.

In some embodiments, the bacterial host cells are further suitable for commercial production, at commercial scale. In some embodiments, the size of the culture is at least about 100 L, at least about 200 L, at least about 500 L, at least about 1,000 L, or at least about 10,000 L. In an embodiment, the culturing may be conducted in batch culture, continuous culture, or semi-continuous culture.

In various embodiments, methods further include recovering the terpene or terpenoid product from the cell culture or from cell lysates. In some embodiments, the culture produces at least about 100 mg/L, or at least about 200 mg/L, or at least about 500 mg/L, or at least about 1 g/L, or at least about 2 g/L, or at least about 5 g/L, or at least about 10 g/L, or at least about 20 g/L, or at least about 30 g/L, or at least about 40 g/L of the terpene or terpenoid product.

In some embodiments, the production of indole (including prenylated indole) is used as a surrogate marker for terpenoid production, and/or the accumulation of indole in the culture is controlled to increase production. For example, in various embodiments, accumulation of indole in the culture is controlled to below about 100 mg/L, or below about 75 mg/L, or below about 50 mg/L, or below about 25 mg/L, or below about 10 mg/L. The accumulation of indole can be controlled by balancing protein expression and activity using the multivariate modular approach as described in U.S. Pat. No. 8,927,241 (which is hereby incorporated by reference), and/or is controlled by chemical means.

Other markers for efficient production of terpene and terpenoids, include accumulation of DOX or ME in the culture media. Generally, the bacterial strains described herein accumulate less of these chemical species, which accumulate in the culture at less than about 5 g/L, or less than about 4 g/L, or less than about 3 g/L, or less than about 2 g/L, or less than about 1 g/L, or less than about 500 mg/L, or less than about 100 mg/L.

The optimization of terpene or terpenoid production by manipulation of MEP pathway genes, as well as manipulation of the upstream and downstream pathways, is not expected to be a simple linear or additive process. Rather, through combinatorial analysis, optimization is achieved through balancing components of the MEP pathway, as well as upstream and downstream pathways. Indole (including prenylated indole) accumulation and MEP metabolite accumulation (e.g., DOX, ME, MEcPP, and/or farnesol) in the culture can be used as surrogate markers to guide this process.

For example, in some embodiments, the bacterial strain has at least one additional copy of dxs and idi expressed as an operon/module; or dxs, ispD, ispF, and idi expressed as an operon or module (either on a plasmid or integrated into the genome), with additional MEP pathway complementation described herein to improve MEP carbon. For example, the bacterial strain may have a further copy of dxr, and ispG and/or ispH, optionally with a further copy of ispE and/or idi, with expressions of these genes tuned to increase MEP carbon and/or improve terpene or terpenoid titer. In various embodiments, the bacterial strain has a further copy of at least dxr, ispE, ispG and ispH, optionally with a further copy of idi, with expressions of these genes tuned to increase MEP carbon and/or improve terpene or terpenoid titer Manipulation of the expression of genes and/or proteins, including gene modules, can be achieved through various methods. For example, expression of the genes or operons can be regulated through selection of promoters, such as inducible or constitutive promoters, with different strengths (e.g., strong, intermediate, or weak). Several non-limiting examples of promoters of different strengths include Trc, T5 and T7. Additionally, expression of genes or operons can be regulated through manipulation of the copy number of the gene or operon in the cell. In some embodiments, expression of genes or operons can be regulated through manipulating the order of the genes within a module, where the genes transcribed first are generally expressed at a higher level. In some embodiments, expression of genes or operons is regulated through integration of one or more genes or operons into the chromosome.

Optimization of protein expression can also be achieved through selection of appropriate promoters and ribosomal binding sites. In some embodiments, this may include the selection of high-copy number plasmids, or single-, low- or medium-copy number plasmids. The step of transcription termination can also be targeted for regulation of gene expression, through the introduction or elimination of structures such as stem-loops.

Expression vectors containing all the necessary elements for expression are commercially available and known to those skilled in the art. See, e.g., Sambrook et al., Molecular Cloning: A Laboratory Manual, Second Edition, Cold Spring Harbor Laboratory Press, 1989. Cells are genetically engineered by the introduction into the cells of heterologous DNA. The heterologous DNA is placed under operable control of transcriptional elements to permit the expression of the heterologous DNA in the host cell.

In some embodiments, endogenous genes are edited, as opposed to gene complementation. Editing can modify endogenous promoters, ribosomal binding sequences, or other expression control sequences, and/or in some embodiments modifies trans-acting and/or cis-acting factors in gene regulation. Genome editing can take place using CRISPR/Cas genome editing techniques, or similar techniques employing zinc finger nucleases and TALENs. In some embodiments, the endogenous genes are replaced by homologous recombination.

In some embodiments, genes are overexpressed at least in part by controlling gene copy number. While gene copy number can be conveniently controlled using plasmids with varying copy number, gene duplication and chromosomal integration can also be employed. For example, a process for genetically stable tandem gene duplication is described in US 2011/0236927, which is hereby incorporated by reference in its entirety.

The terpene or terpenoid product can be recovered by any suitable process, including partitioning the desired product into an organic phase or hydrophobic phase. Alternatively, the aqueous phase can be recovered, and/or the whole cell biomass can be recovered, for further processing. The production of the desired product can be determined and/or quantified, for example, by gas chromatography (e.g., GC-MS). The desired product can be produced in batch or continuous bioreactor systems. Production of product, recovery, and/or analysis of the product can be done as described in US 2012/0246767, which is hereby incorporated by reference in its entirety. For example, in some embodiments, product oil is extracted from aqueous reaction medium using an organic solvent, such as an alkane such as heptane or dodecane, followed by fractional distillation. In other embodiments, product oil is extracted from aqueous reaction medium using a hydrophobic phase, such as a vegetable oil, followed by organic solvent extraction and fractional distillation. Terpene and terpenoid components of fractions may be measured quantitatively by GC/MS, followed by blending of fractions to generate a desired product profile.

In various embodiments, the recovered terpene or terpenoid is incorporated into a product (e.g., a consumer or industrial product). For example, the product may be a flavor product, a fragrance product, a sweetener, a cosmetic, a cleaning product, a detergent or soap, or a pest control product. For example, in some embodiments, the product recovered comprises nootkatone, and the product is a flavor product selected from a beverage, a chewing gum, a candy, or a flavor additive, or the product is an insect repellant or insecticide. In some embodiments, the oxygenated product is steviol or a steviol glycoside (e.g., RebM), which is provided as a sweetener, or is incorporated into ingredients, flavors, beverages or food products.

The invention further provides methods of making products such as foods, beverages, texturants (e.g., starches, fibers, gums, fats and fat mimetics, and emulsifiers), pharmaceutical products, tobacco products, nutraceutical products, oral hygiene products, and cosmetic products, by incorporating the terpene or terpenoids produced herein. The higher yields of such species produced in embodiments of the invention can provide significant cost advantages as well as sustainability.

In other aspects, the invention provides bacterial cells, such as *E. coli*, having one or more genetic modifications that increase MEP carbon. In various embodiments, the bacterial cells produce isopentenyl diphosphate (IPP) and dimethylallyl diphosphate (DMAPP) through the MEP pathway, and convert the IPP and DMAPP to a terpene or terpenoid product through a downstream synthesis pathway. The downstream synthesis pathway is generally a recombinant pathway, and may comprise a prenyl transferase, a terpene synthase, and optionally one or more cytochrome P450 enzymes and cytochrome P450 reductase enzymes (for example, each as described above). Further, to improve MEP carbon, the *E. coli* has one or more of the following genetic modifications:

(1) decreased expression or activity of IspB, optionally by modification of the RBS, and optionally where the six-base SD sequence in the ispB gene is changed to CGTGCT or CGTGCC, or a modification thereof having one or two nucleotide changes from CGTGCT or CGTGCC;

(2) a deletion or inactivation of all or part of the iscR gene, and a constitutive or inducible promoter to drive expression of the genes remaining in the isc operon (e.g., iscSUA) under conditions used for terpene or terpenoid production;

(3) a ryhB deletion or inactivation;

(4) MEP enzyme expression or activity is altered or balanced such that DOX and/or ME do not accumulate above about 2 g/L or about 1 g/L;

(5) MEP pathway complementation comprising a dxr gene (optionally with ispD, ispE, and/or ispF) and an ispG and/or ispH gene, where the IspG or IspH is optionally modified to increase enzyme activity; and wherein the IspG optionally has one or more mutations at positions selected from V30, S32, T34, N35, R37, V59, V61, S62, V63, L83, V84, C104, L105, P131, I132, I134, A138, K143, F176, K177, V178, V180, A182, L205, I207, A210, G212, A213, L236, V238, A241, A242, D243, R259, S262, R263, I265, N266, F267, I268, A269, T272, 5274, Q276, E277, F278, D289, S301, I302, I303, V306; and optionally modifications at a plurality of positions selected from: (1) V30, S32, T34, N35, R37; or (2) V59, V61, S62, V63, L83, V84; or (3) C104, L105, S301, I302, I303, V306; or (4) P131, I132, I134, A138, K143; or (5) F176, K177, V178, V180, A182; or (6) L205, I207, A210, G212, A213; or (7) L236, V238, A241, A242, D243; or (8) R259, S262, R263, I265, N266; or (9) F267, I268, A269, T272, S274, Q276, E277, F278, D289; and optionally one, two, three, or all of L205V, A210S, G212T, and A213I; and (6) a mutation in pgi (glucose-6-phosphate isomerase) supporting increased terpenoid titer or increases in MEP carbon.

In some embodiments, the bacterial strain has at least one additional copy of dxs and idi expressed as an operon/module; or dxs, ispD, ispF, and idi expressed as an operon or module (either on a plasmid or integrated into the genome). Further, the bacterial strain may have a further copy of dxr, ispE, and ispG and/or ispH, with expressions of these genes tuned to increase MEP carbon and/or improve terpene or terpenoid titer.

In various embodiments, the bacterial strains comprises at least 2, at least 3, at least 4, at least 5, or all 6 modifications defined by (1) to (6) above.

Genes can be overexpressed by complementation with recombinant genes, or the endogenous genes can be modified to alter expression, as disclosed elsewhere herein.

The bacterial strain is a bacteria selected from *Escherichia* spp., *Bacillus* spp., *Corynebacterium* spp., *Rhodobacter* spp., *Zymomonas* spp., *Vibrio* spp., and *Pseudomonas* spp. For example, the bacterial strain is a species selected from *Escherichia coli, Bacillus subtilis, Corynebacterium glutamicum, Rhodobacter capsulatus, Rhodobacter sphaeroides, Zymomonas mobilis, Vibrio natriegens*, or *Pseudomonas putida*. In some embodiments, the bacterial strain is *E. coli*.

Aspects and embodiments of the invention are further demonstrated below with reference to the following Examples.

EXAMPLES

Figure 2:
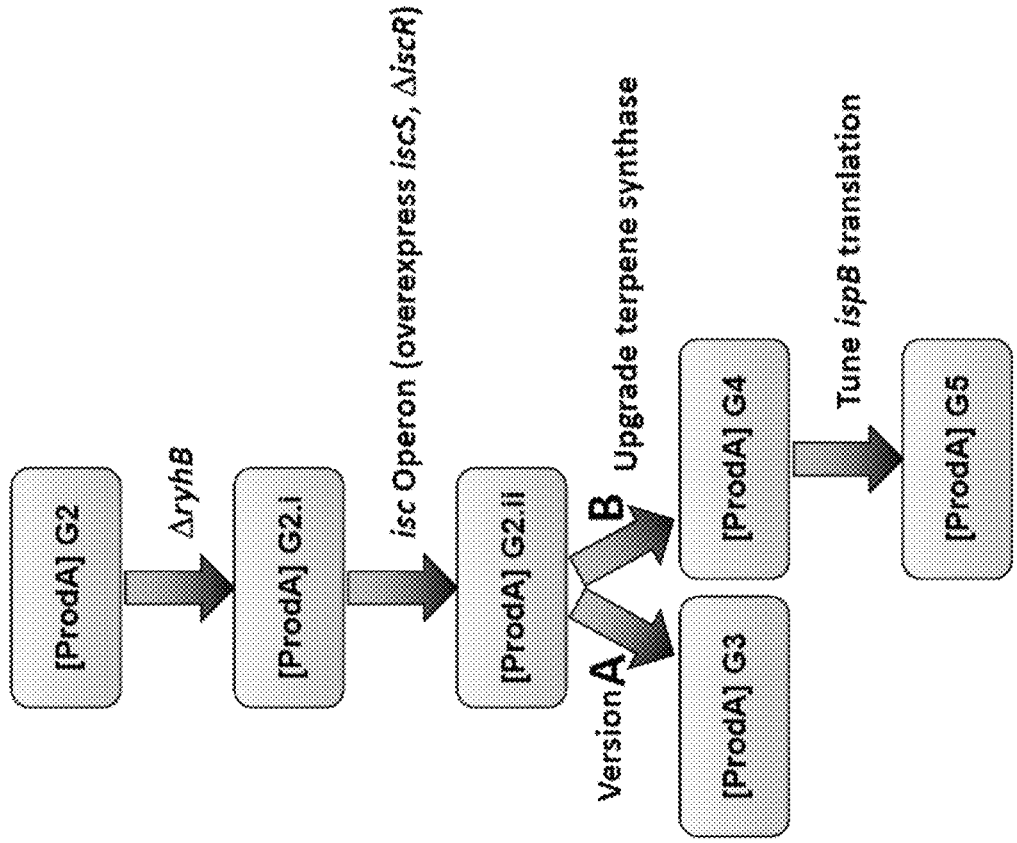
FIG. 2 illustrates genetic modifications to *E. coli* strain chassis to improve terpenoid production via the MEP pathway for an exemplary terpenoid product (Product A).
Figure 3:
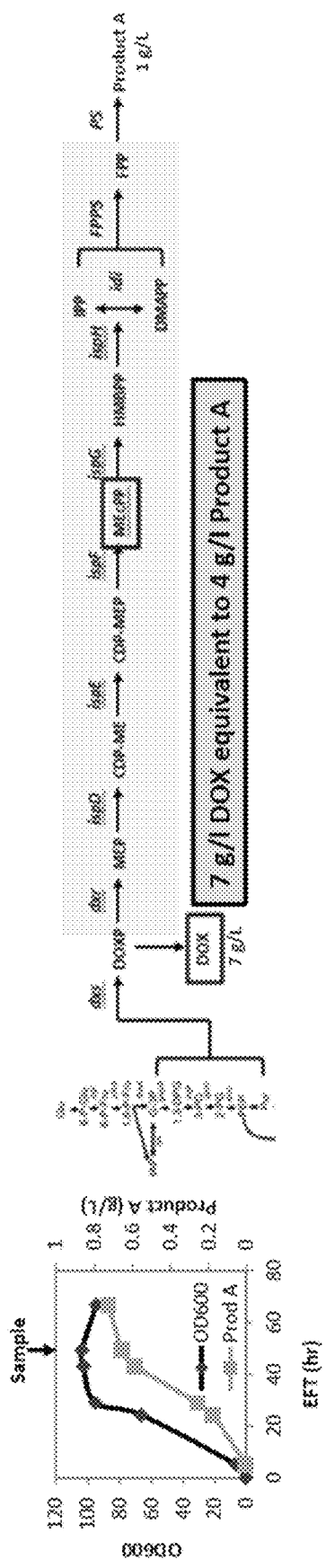
FIG. 3 shows the modifications to the Product A strain in going from Strain G2 to Strain G4 (see FIG. 2). These modifications enable the carbon to move 'downstream' in the MEP biochemical pathway, pushing the intermediate product pools from DOXP (and extracellular DOX) to MEP (and extracellular ME). The extracellular accumulation of large pools of MEP pathway intermediates can be used to inform engineering designs intending to push carbon flux down the pathway and on to MEcPP.
Figure 3:
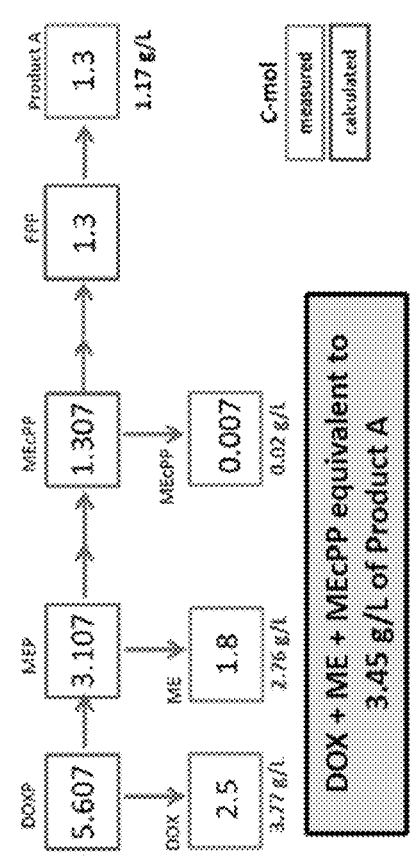
Figure 3:
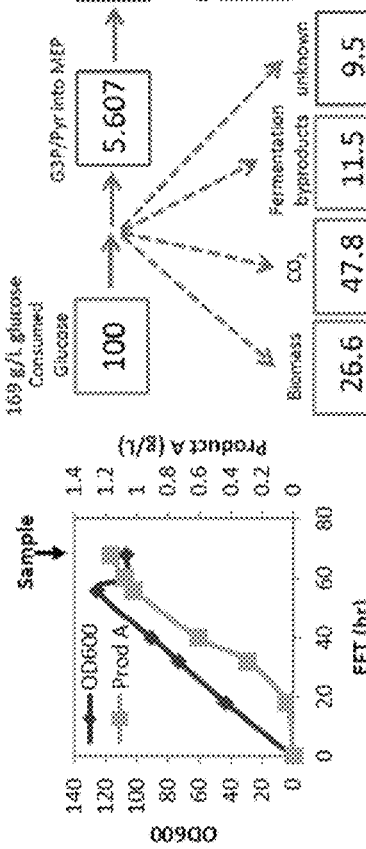

Example 1: Increased Availability of Fe—S Proteins Shifts Accumulation from DOX to ME As shown in FIG. 3, G2 (as described in FIG. 2) produces key extracellular metabolites (DOX+ME+MEcPP) equivalent to 3.45 g/L of terpenoid product. This compares to 7 g/L of primarily DOX in the strain not containing modifications to increase Fe—S proteins. G4 also had a 56% higher accumulation of the terpenoid product. Genetic modifications include ΔryhB, ΔiscR with overexpression of the isc operon.

Figure 4:
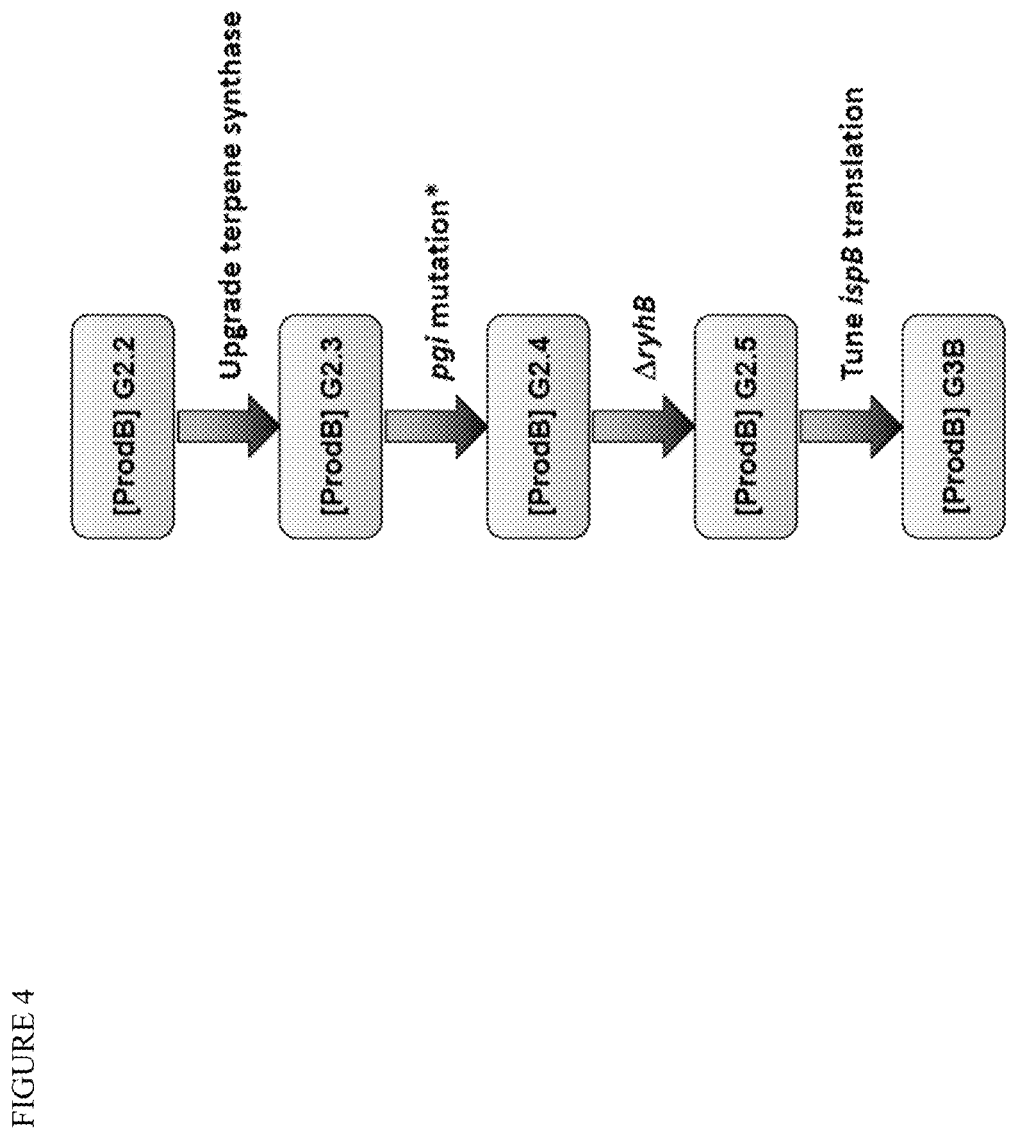
FIG. 4 shows genetic modifications to *E. coli* strain chassis to improve terpenoid production via the MEP pathway for Product B. The pgi mutant modification was identified in a high-production clone.

Similar results were obtained for an *E. coli* strain engineered to produce another terpenoid product (Product B), and showing DOX+ME+MEcPP equivalent to 3.26 g/L of the terpenoid product. Additional modifications include a modification to pgi, which lead to a 1.4× improvement, and tuning of ispB translation. See FIG. 4.

Figure 5:
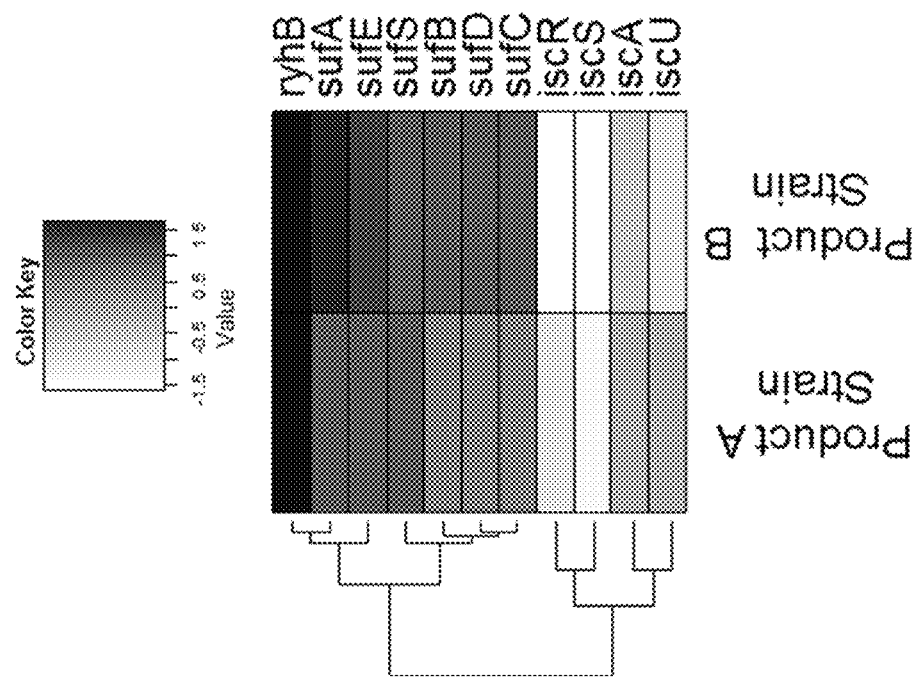
FIG. 5 shows results from a transcriptome profiling experiment providing evidence for the involvement of ryhB and the isc operon. The expression of ryhB is upregulated, and the isc operon is generally down-regulated, in *E. coli* in response to the installation of a downstream terpenoid pathway for the production of Product A or Product B.

As shown in FIG. 5, transcriptome sequencing and analysis comparing engineered product strains to wild-type *E. coli* generated strong evidence for involvement of ryhB and the isc operon in the altered phenotypes of the product strains. The former gene is strongly upregulated in our engineered strains, while the iscR regulatory gene is very strongly down-regulated.

Figure 6:
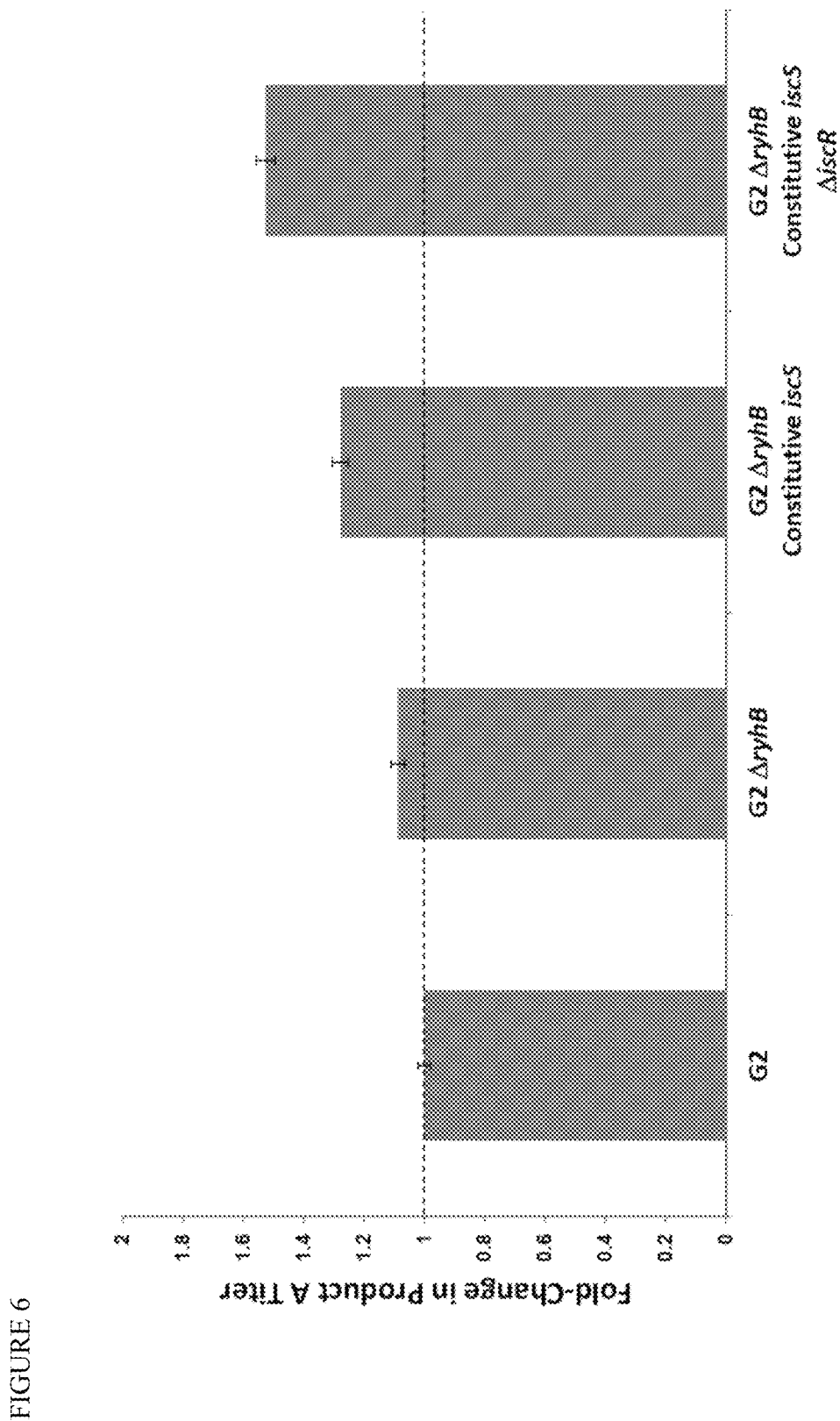
FIG. 6 shows the combined effect of ryhB and isc operon modifications. Given the importance of iron and iron-sulphur (Fe—S) cluster biochemistry in MEP terpenoid metabolism, a series of modifications to the production chassis was performed to increase titer of product (Product A). In sequential order, the G2 Product A chassis had the ryhB deleted, then the wild-type promoter of iscS was replaced with a constitutive promoter sequence, and the native iscR gene was deleted. With each modification, titer of product A increases.

As shown in FIG. 6, sequential modification via deletion of ryhB, switch to constitutive overexpression for iscSUA, and deletion of iscR results in strains with steadily increasing product titers.

Example 2: Engineering ispG to Improve MEP Pathway Flux

Figure 7A:
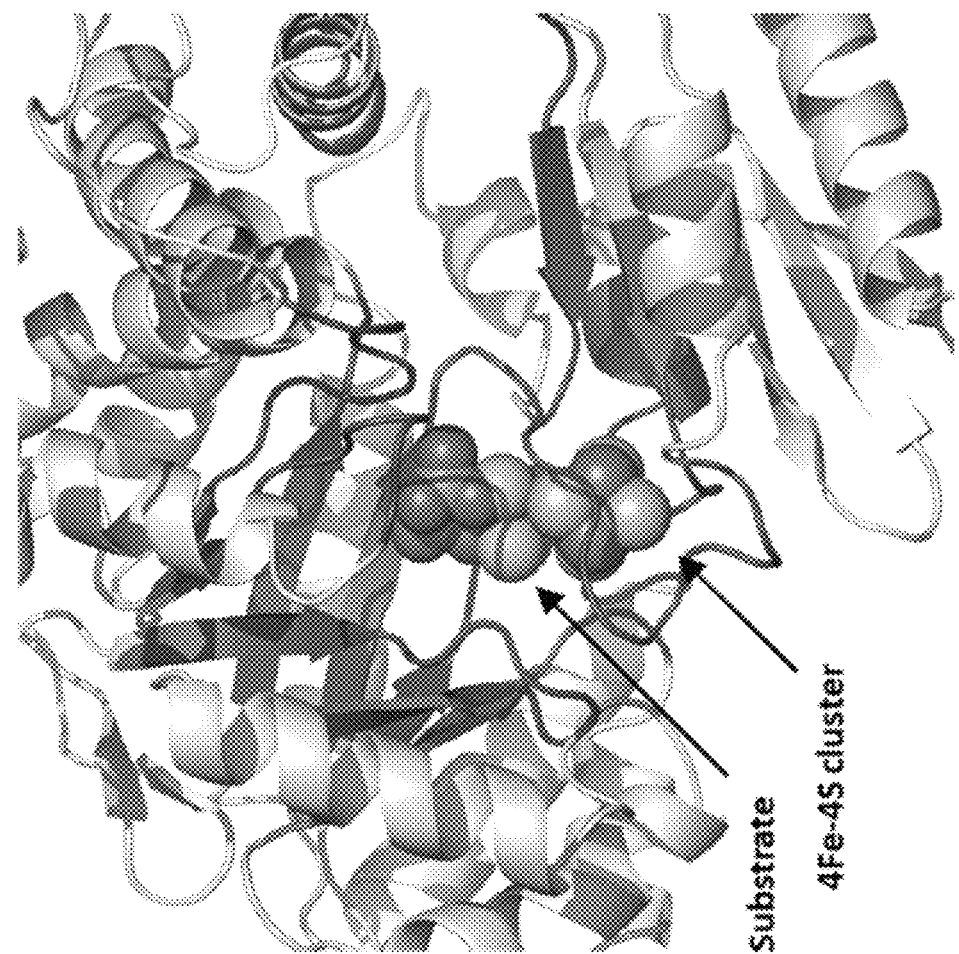

A series of libraries where the active site of ispG was combinatorially varied were created and tested in vivo by replacing the wild-type ispG gene with mutated versions. ispG engineering may improve kinetics, stability, and robustness of the enzyme, to relieve the impact of Fe—S cluster biochemistry on the flux through the MEP pathway. Nine active site combinatorial libraries were designed to target substrate and iron-sulfur cluster binding sites using sequence alignments of ~1000 diverse ispG orthologs (FIG. 7A, 7B).

Figure 8:
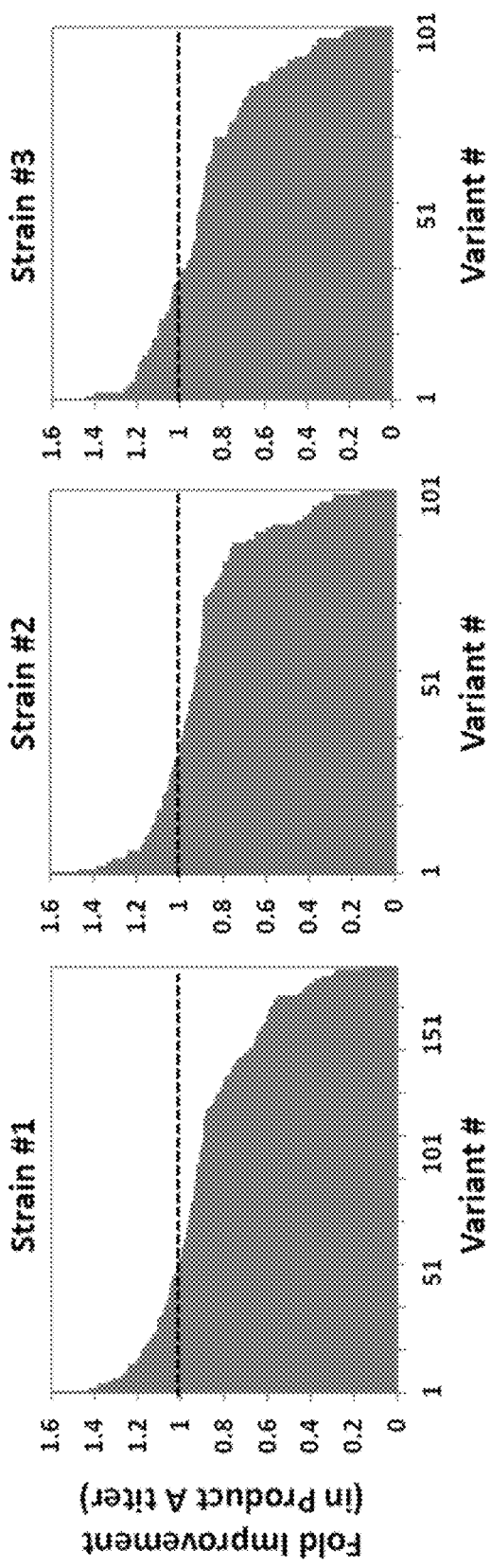
FIG. 8 shows screening of the mutation libraries of wild-type *E. coli* ispG gene, to replace the wild-type gene in three strains that make Product A. Preliminary screening of the integrated libraries resulted in 20-40% of the introduced variants giving improved product titers, with up to 1.5× increase in terpenoid product observed.

FIG. 8 shows the results of a primary screen of ispG combinatorial library for increased sesquiterpene product titer in two background strains. Screening is conducted in 96 DWP at 37° C. for 48 hours. Similar performance was seen using both strain backgrounds (with or without ispH overexpression) with a total of ~30 variants showing 1.2 to 1.45× improvements in terpenoid product titers.

Figure 9:
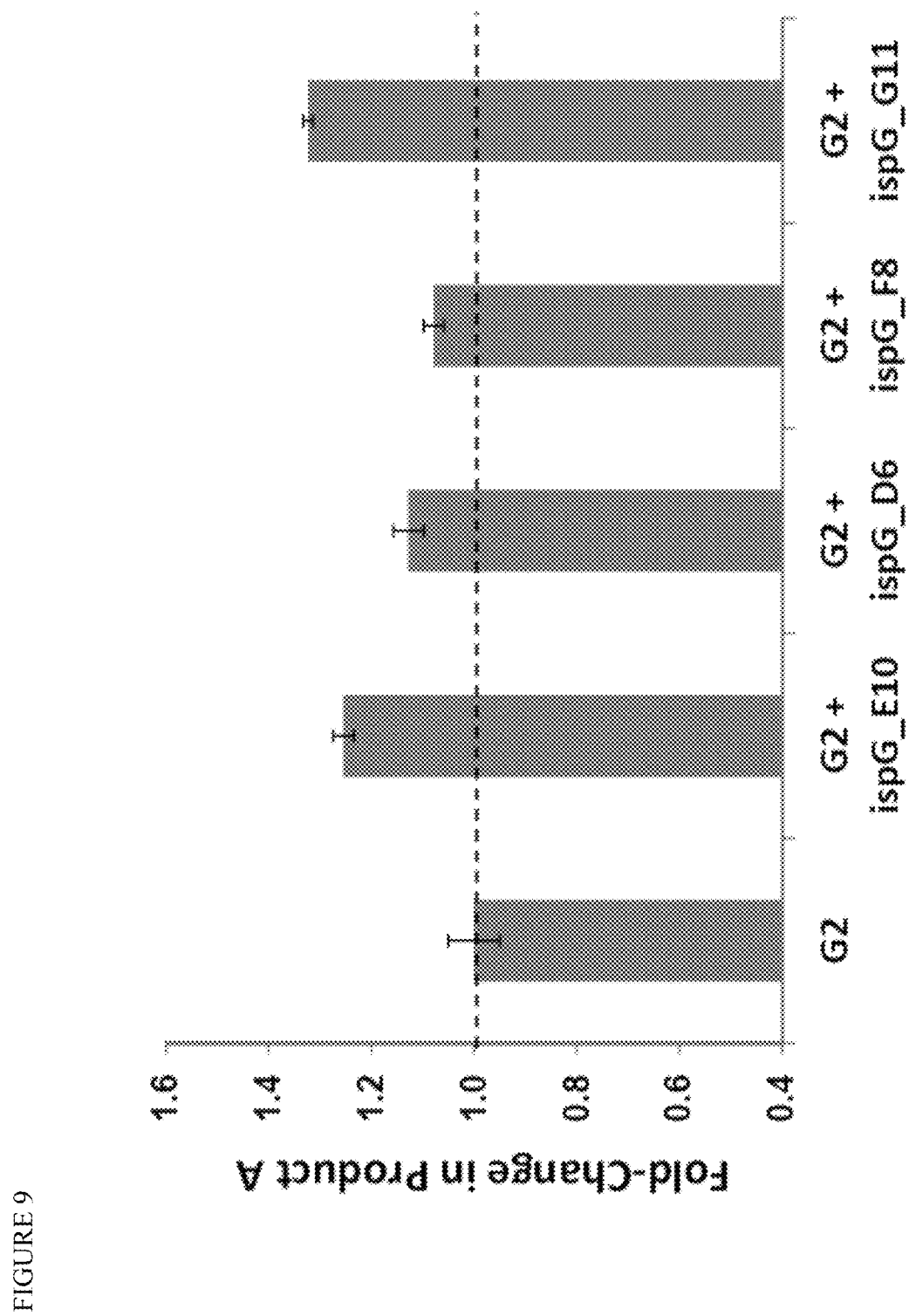
FIG. 9 shows the results of validation and secondary re-screening of leads resulting from the primary screen. The G11 variant was incorporated into production chassis for both Products A and B.

Lead variants were rescreened, with the results shown in FIG. 9. Two ispG variants gave ~1.2× improvement in terpene product titer over the strain engineered for increased availability of Fe—S proteins. The lead variant, G11, has the following mutations: L205V, A210S, G212T, and A213I.

Figure 10:
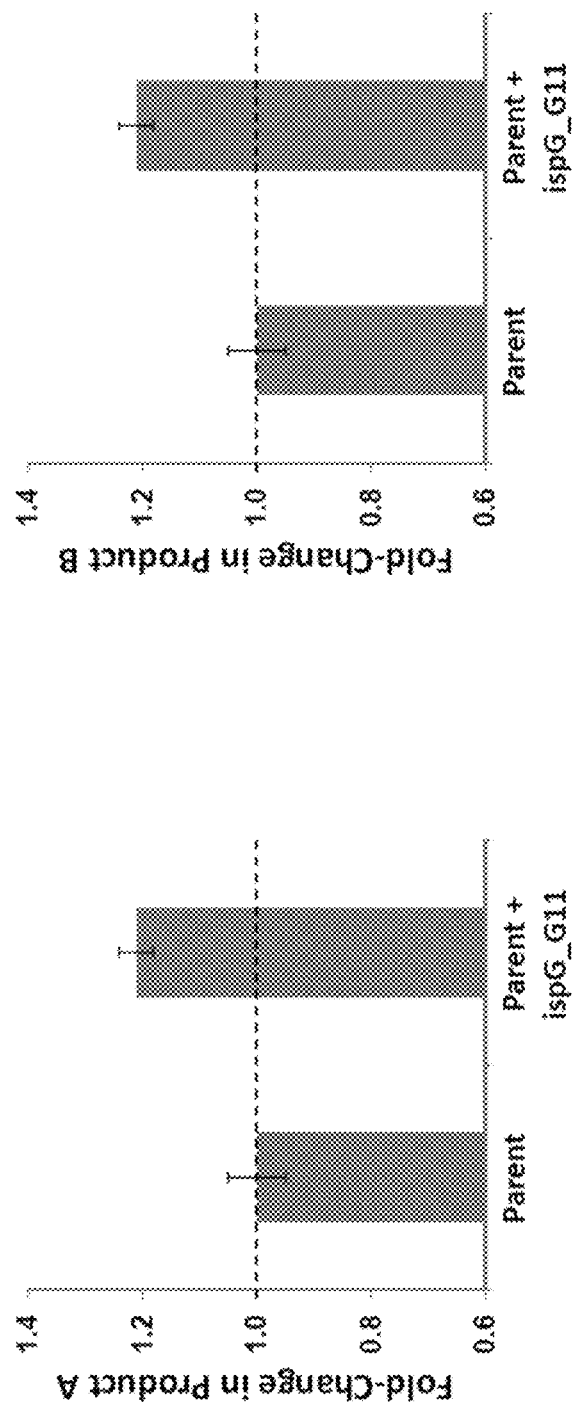
FIG. 10 shows results upon supplementing the wild-type ispG gene in the production strains with the selected mutated version. The supplementation results in a 20% increase in product titer. The complete translation of the improvement regardless of the terpenoid product suggests the possibility of a 'universal chassis' that can support the high-level production of any terpenoid via the MEP pathway.

The lead variant is integrated into lead terpenoid producing strains, and the product titers shown in FIG. 10. Integration of ispG Lib6 G11 led to a 1.2× improvement in production in both strains.

Example 3: ispB Translation Engineering

The ispB gene encodes an octaprenyl diphosphate synthase that controls the synthesis of ubiquinone and thus directly competes with FPP synthase for IPP and DMAPP precursors. Decreasing the amount of ispB enzyme in the cell by modifying the ispB RBS sequence and tuning down translation of the mRNA could shift carbon flux toward the recombinant terpenoid pathway.

Figure 11:
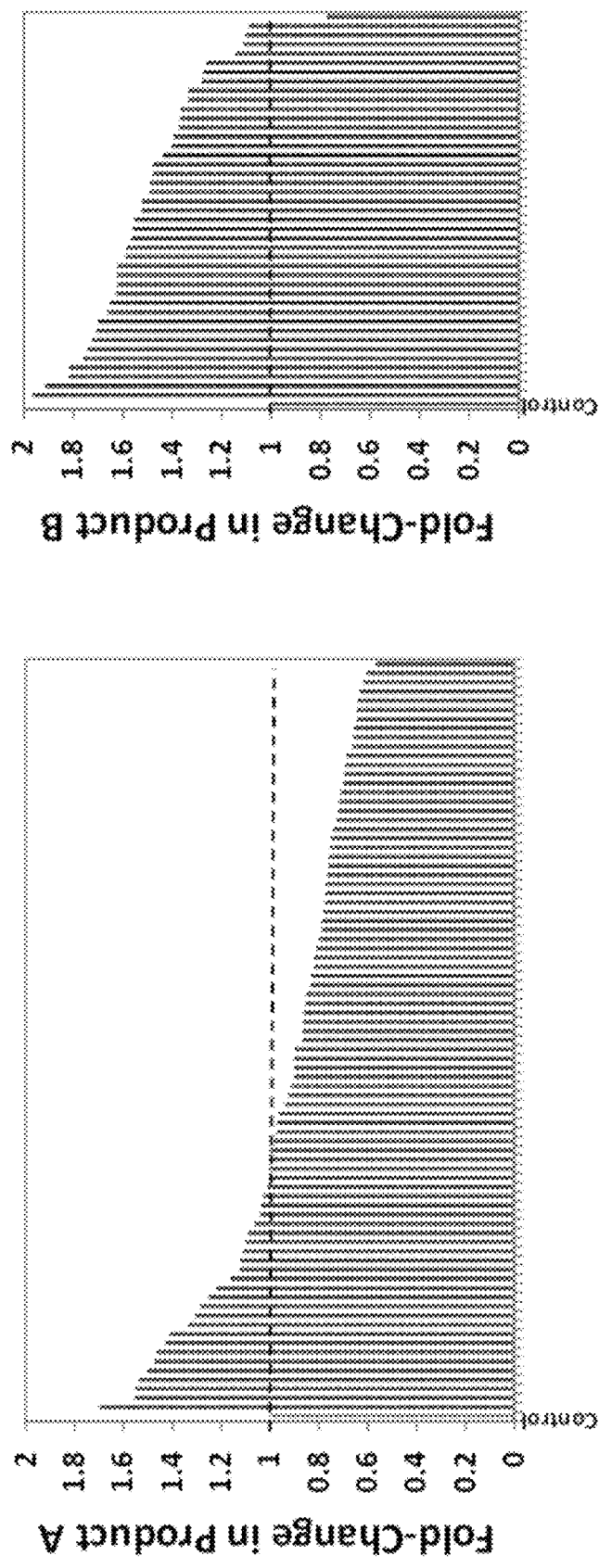
FIG. 11 shows tuning the translation rate of ispB via modification of the native RBS sequence, which improves the production of terpenoid product. Various mutants of the wild-type (WT) ispB RBS (ribosome binding site) were introduced over the native ispB RBS to tune protein translation. These RBS changes impact terpenoid production, some of them resulting in improved production. Several hits were identified from the primary screening, giving strains with improvement of 1.7× for Product A and 2× for Product B. The left-most column is for the parental control, which sets the value of 1. Lead hits are repeated and validated, fully sequenced, and then transferred into the lead generation of each product strain.
Figure 12:
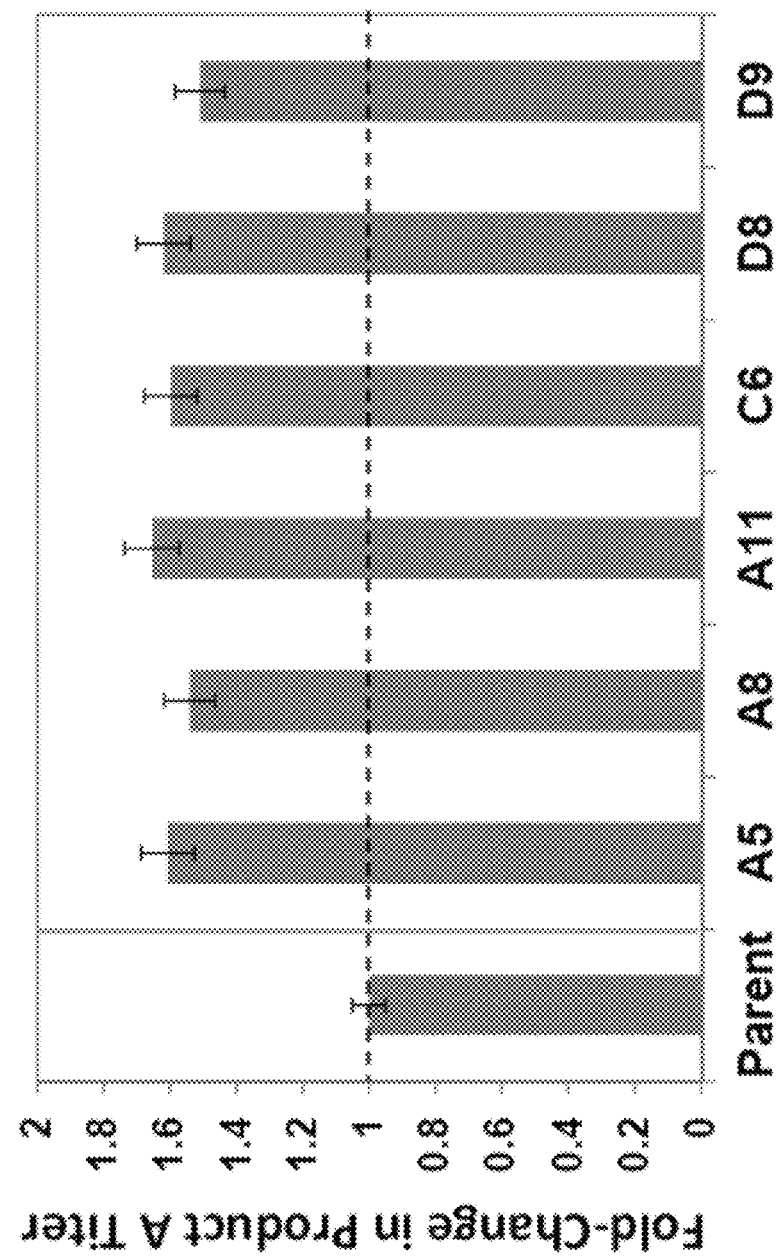
FIG. 12 shows four mutant strains validated through secondary screening with replication, confirming the improvement observed in the primary screen of ispB RBS.

As shown in FIG. 11, several potential hits are identified from primary screening of the ispB RBS libraries yielding up to 1.7 fold improvement in terpene/terpenoid production. Lead hits were validated as shown in FIG. 12. Two unique hits were identified that yielded a 1.5-fold improvement in terpenoid production, having the following SD sequences: CGTGCT and CGTGCC.

Example 4: MEP Pathway Complementation

As shown in FIG. 13, overexpression of dxr by itself or in combination with ispD, ispE, and ispF decreases production by up to 2-fold. Addition of ispG-ispH returns production back to original levels.

Figure 14:
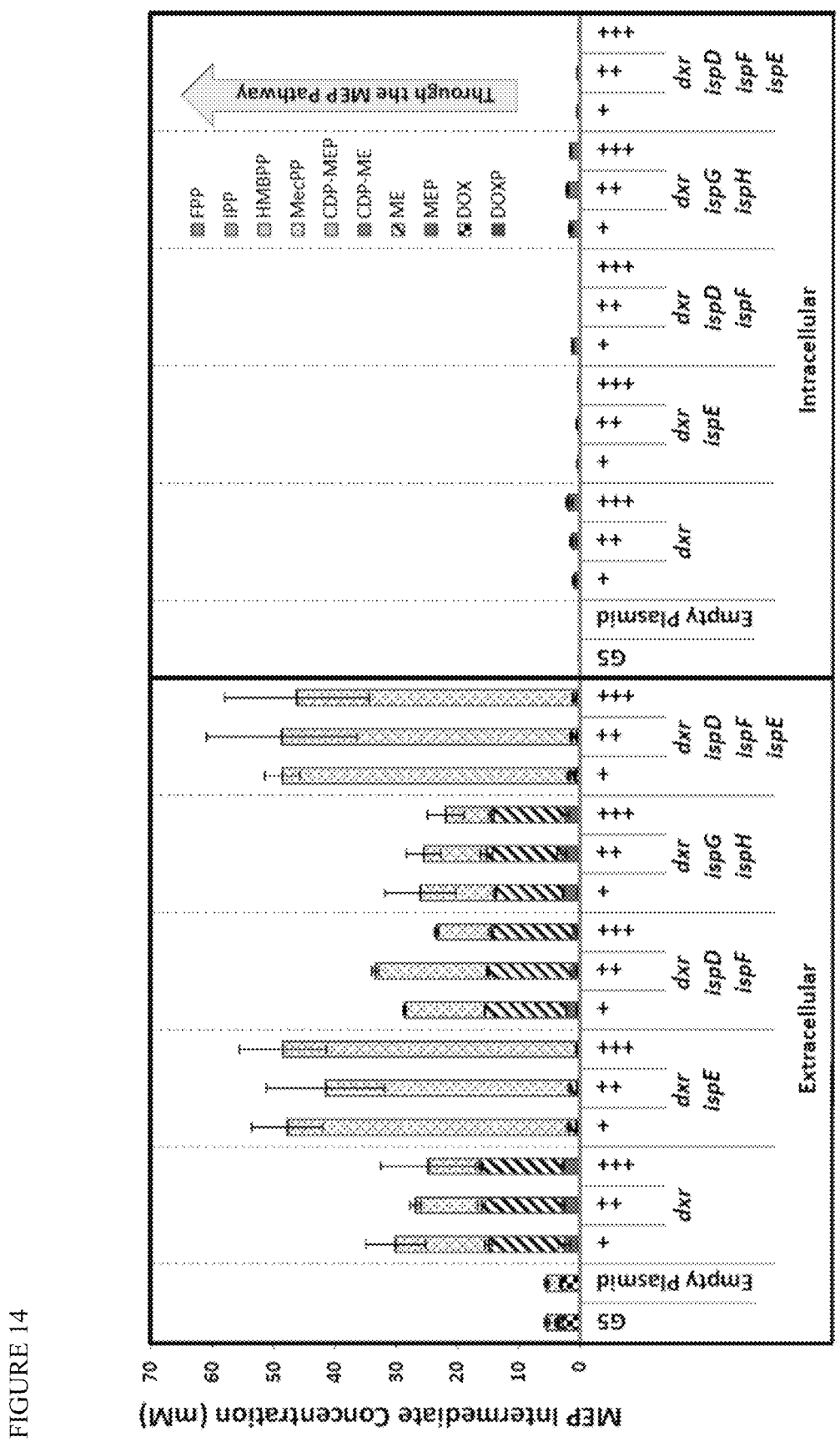
FIG. 14 shows that, though titer drops, more carbon goes into MEP pathway. While the MEP pathway complementation work showed that Product A titer dropped or stayed the same in response to gene expression changes, the intermediate MEP pathway metabolites increased significantly more in concentration. MEP carbon metabolites were quantified via liquid chromatography and mass spectrometry against authentic standards, and found to significantly increase in complemented strains compared to control G5 strains. The resulting metabolite concentrations are expressed in terms of molarity, to focus on the flow of carbon molecules through the MEP pathway to the desired product. The majority of MEP intermediates are observed outside the cell, with DOX, ME, and MEcPP representing the majority; the major intracellular product is CDP-ME, with increasing accumulation observed in complemented strains. While dxr overexpression caused the Product A titer to drop by 2×, the amount of carbon entering the MEP pathway and accumulating as intermediates went up 6×; that is, more carbon is entering the MEP pathway, but less of it is getting out. Moreover, while the G5 parent accumulated mostly DOX (and some MEcPP), the increase in dxr (which converts DOXP to MEP) shifts the carbon down the pathway, resulting in more carbon pooling extracellularly as ME and MEcPP. Increasing ispE expression on top of dxr further increase the amount of carbon in the MEP pathway to almost 10× over the G5 parent, and shifted almost all of that carbon downstream to MEcPP. Interestingly, overexpressing ispG and ispH in addition to dxr gives you a very similar intermediate profile to overexpressing dxr only, though the product titer is doubled in the former instance.
Figure 15:
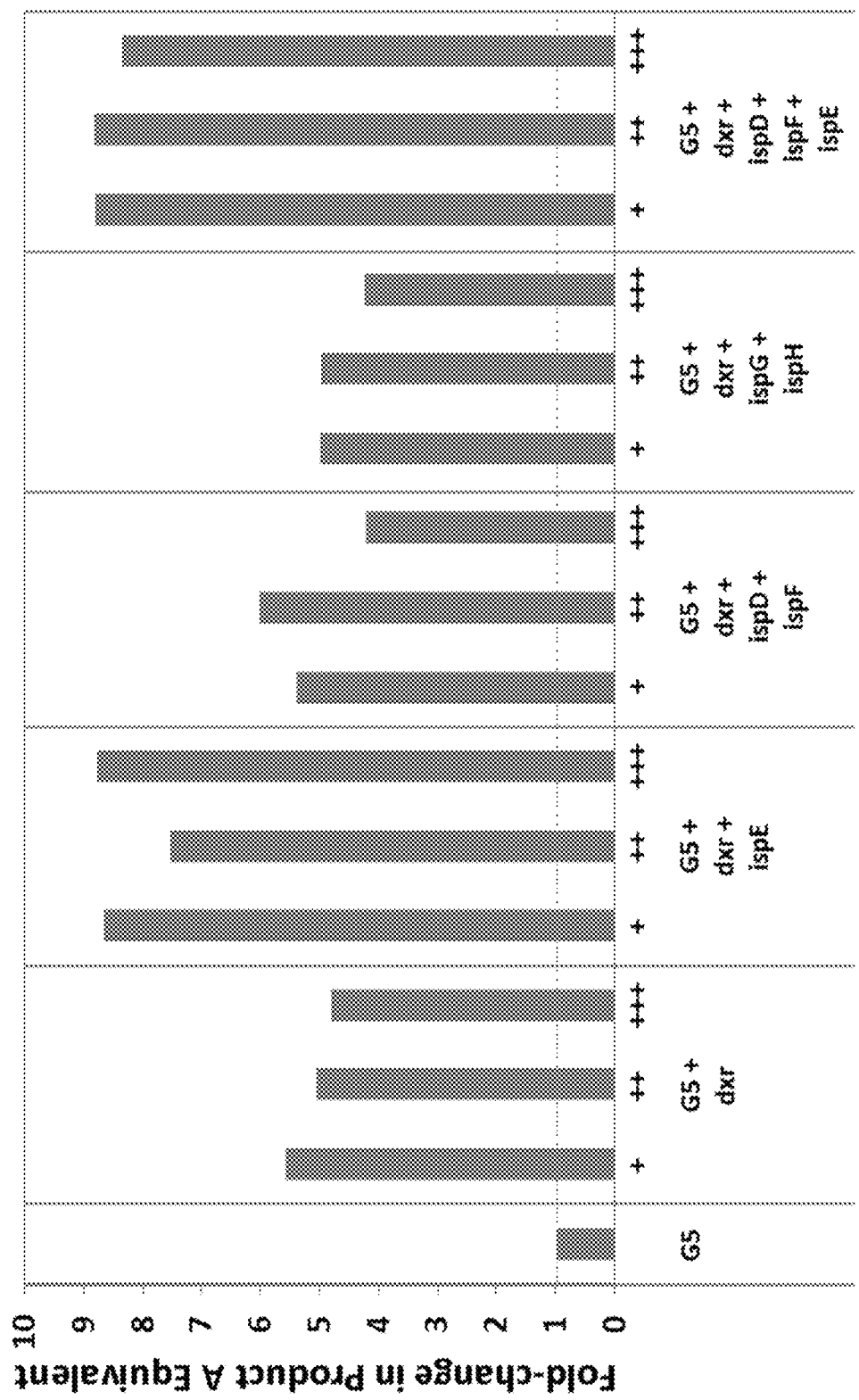
FIG. 15 shows the total amount of Product A that would be produced if all carbon accumulating in the MEP pathway in FIG. 14 was successfully converted through to final product. The data shows production potential of the G5 strain complemented with an empty plasmid versus the same plasmid backbone expressing MEP pathway genes (with varied expression level increasing from + to +++). Converting the total amount of carbon in the MEP pathway (quantified as in FIG. 14) into Product A Equivalents shows that the carbon flux through the pathway increases with complementation, with almost 9× more Product A potential made possible in these strains.

As shown in FIG. 14, metabolomics analysis shows that overexpression of dxr without ispE leads to accumulation of extracellular ME and intracellular CDP-ME. Overexpressing ispE shifts metabolite pools from ME and CDP-ME to MEcPP. In this example, strains are grown in 96-well plates at 37 dC for 48 hrs. At the endpoint, the cell cultures are measured for OD600, then are split into two samples; the first is extracted with Ethyl Acetate to analyze and quantify Product A, while the second is centrifuged to pellet the cells, and the supernatant is analyzed for extracellular MEP metabolites while the cell pellet is further processed to extract intracellular MEP metabolites. The terpenoid product-containing organic phase sample is analyzed via gas chromatography and mass spectrometry (GC/MS), while the extracellular and intracellular metabolite samples are separated and analyzed via liquid chromatography and mass spectrometry (LC/MS). The LC/MS detector is a triple-quadrupole instrument, enabling accurate quantification of MEP metabolites against authentic standards. The resulting metabolite concentrations are expressed in terms of molarity, to focus on the flow of carbon molecules through the MEP pathway to the desired product.

As shown in FIG. 15, metabolomics analysis of Product A G5 strains with MEP complementation with dxr or dxr-ispE further shows that the increased MEP flux potential in the resulting strains translates into more potential Product A titer. The measured product and MEP metabolite concentrations for these strain cultures are converted to molarity, and the carbon equivalent of each MEP metabolite in terms of Product A is calculated; i.e., one MEcPP molecule contains 5 carbons, so each one translates into 1 molecule of isopentenyl diphosphate (IPP, with 5 carbons as well), or ⅓ of a sesquiterpene Product A molecule (with 15 carbons). In this way, the potential total of Product A produced by this strain—when carbon is successfully pulled downstream through MEcPP—can be calculated. With balanced expression between MEP genes, up to 12× more product A could result.

LISTING OF SEQUENCES

SEQ ID NO: 1 (modified Shine-Dalgarno sequence 1):
CGTGCT

SEQ ID NO: 2 (modified Shine-Dalgarno sequence 2):
CGTGCC

SEQ ID NO: 3 (*E. coli* IspB)
MNLEKINELTAQDMAGVNAAILEQLNSDVQLINQLGYYIVSGGGKRIRP
MIAVLAARAVGYEGNAHVTIAALIEFIHTATLLHDDVVDESDMRRGKAT
ANAAFGNAASVLVGDFIYTRAFQMMTSLGSLKVLEVMSEAVNVIAEGEV
LQLMNVNDPDITEENYMRVIYSKTARLFEAAAQCSGILAGCTPEEEKGL
QDYGRYLGTAFQLIDDLLDYNADGEQLGKNVGDDLNEGKPTLPLLHAMH
HGTPEQAQMIRTAIEQGNGRHLLEPVLEAMNACGSLEWTRQRAEEEADK
AIAALQVLPDTPWREALIGLAHIAVQRDR SEQ ID NO: 4 (*E. coli* Dxr)
MKQLTILGSTGSIGCSTLDVVRHNPEHFRVVALVAGKNVTRMVEQCLEF
SPRYAVMDDEASAKLLKTMLQQQGSRTEVLSGQQAACDMAALEDVDQVM
AAIVGAAGLLPTLAAIRAGKTILLANKESLVTCGRLFMDAVKQSKAQLL
PVDSEHNAIFQSLPQPIQHNLGYADLEQNGVVSILLTGSGGPFRETPLR
DLATMTPDQACRHPNWSMGRKISVDSATMMNKGLEYIEARWLFNASASQ
MEVLIHPQSVIHSMVRYQDGSVLAQLGEPDMRTPIAHTMAWPNRVNSGV
KPLDFCKLSALTFAAPDYDRYPCLKLAMEAFEQGQAATTALNAANEITV
AAFLAQQIRFTDIAALNLSVLEKMDMREPQCVDDVLSVDANAREVARKE
VMRLAS SEQ ID NO: 5 (*E. coli* IspG)
MHNQAPIQRRKSTRIYVGNVPIGDGAPIAVQSMTNTRTTDVEATVNQIK
ALERVGADIVRVSVPTMDAAEAFKLIKQQVNVPLVADIHFDYRIALKVA
EYGVDCLRINPGNIGNEERIRMVVDCARDKNIPIRIGVNAGSLEKDLQE
KYGEPTPQALLESAMRHVDHLDRLNFDQFKVSVKASDVFLAVESYRLLA
KQIDQPLHLGITEAGGARSGAVKSAIGLGLLLSEGIGDTLRVSLAADPV
EEIKVGFDILKSLRIRSRGINFIACPTCSRQEFDVIGTVNALEQRLEDI
ITPMDVSIIGCVVNGPGEALVSTLGVTGGNKKSGLYEDGVRKDRLDNND
MIDQLEARIRAKASQLDEARRIDVQQVEK SEQ ID NO: 6 (*E. coli* IspH)
MQILLANPRGFCAGVDRAISIVENALAIYGAPIYVRHEVVHNRYVVDSL
RERGAIFIEQISEVPDGAILIFSAHGVSQAVRNEAKSRDLTVFDATCPL
VTKVHMEVARASRRGEESILIGHAGHPEVEGTMGQYSNPEGGMYLVESP
DDVWKLTVKNEEKLSFMTQTTLSVDDTSDVIDALRKRFPKIVGPRKDDI
CYATTNRQEAVRALAEQAEVVLVVGSKNSSNSNRLAELAQRMGKRAFLI
DDAKDIQEEWVKEVKCVGVTAGASAPDILVQNVVARLQQLGGGEAIPLE
GREENIVFEVPKELRVDIREVD SEQ ID NO: 7 (*Brucella abortus* Deoxyxylulose-5-phosphate Reductoisomerase-like (DRL))
MTTNVALVGLARDLAARAETGKPIRIGLIGAGEMGTDIVTQVARMQGIE

VGALSARRLPNTFKAIRTAYGDEENAREATTESAMTRAIEAGKIAVTDD

NDLILSNPLIDVIIDATGIPEVGAETGIAAIRNGKHLVMMNVEADVTIG

PYLKAQADKQGVIYSLGAGDEPSSCMELIEFVSALGYEVVSAGKGKNNP

LNFDATPDDYRQEADRRNMNVRLLVEFIDGSKTMVEMAAIANATGLVPD

IAGMHGPRASIDQLSHTLIPQAEGGVLSKSGVVDYSIGKGVSPGVFVVA

KMDHPRLNERLEDLKIGKGPYFTFHRPYHLTSLEVPLTVARVVLHGKTD

MVPLPKPVAEVCAVAKKDMQPGEHLDAIGQYCYRSWIMTVPEARAAKAI

PCGLLQNGTVIAPIKKGELITYANAAPQPGSRIAELRALQDAMLGQ

SEQ ID NO: 8 (*E. coli* ispE)
MRTQWPSPAKLNLFLYITGQRADGYHTLQTLFQFLDYGDTISIELRDDG

DIRLLTPVEGVEHEDNLIVRAARLLMKTAADSGRLPTGSGANISIDKRL

PMGGGLGGGSSNAATVLVALNHLWQCGLSMDELAEMGLTLGADVPVFVR

GHAAFAEGVGEILTPVDPPEKWYLVAHPGVSIPTPVIFKDPELPRNTPK

RSIETLLKCEFSNDCEVIARKRFREVDAVLSWLLEYAPSRLTGTGACVF

AEFDTESEARQVLEQAPEWLNGFVAKGANLSPLHRAML

The invention claimed is:

1. A bacterial strain comprising:
   a recombinant terpenoid synthesis pathway comprising a terpene synthase, the bacterial strain producing isopentenyl diphosphate (IPP) and dimethylallyl diphosphate (DMAPP) through the methylerythritol phosphate (MEP) pathway, and converting the IPP and DMAPP to a terpene or terpenoid through the recombinant terpenoid synthesis pathway; and
   one or more genetic modifications that increase MEP carbon, said genetic modifications comprising a ryhB deletion or inactivation.

2. The bacterial strain of claim 1, wherein the strain is a bacterium selected from *Escherichia* spp., *Bacillus* spp., *Rhodobacter* spp., *Zymomonas* spp., or *Pseudomonas* spp.

3. The bacterial strain of claim 1, wherein the strain overexpresses Dxr.

4. The bacterial strain of claim 3, wherein Dxr is overexpressed by complementation with a recombinant gene or operon comprising dxr.

5. The bacterial strain of claim 1, wherein the strain overexpresses IspE.

6. The bacterial strain of claim 5, wherein IspE is overexpressed by complementation with a recombinant gene or operon comprising ispE.

7. The bacterial strain of claim 1, wherein the strain overexpresses ispG and/or ispH.

8. The bacterial strain of claim 7, wherein ispG and/or ispH are overexpressed by complementation with a recombinant gene or operon comprising ispG and/or H.

9. The bacterial strain of claim 8, wherein the strain has a modified IspG enzyme having increased activity with respect to wild type *E. coli* IspG.

10. The bacterial strain of claim 9, wherein the IspG enzyme has one, two, three or all of the following mutations: L205V, A210S, G212T, and A213I with respect to SEQ ID NO: 5.

11. The bacterial strain of claim 1, wherein the bacterial strain has at least one additional copy of dxs and idi expressed as an operon or module.

12. The bacterial strain of claim 11, wherein the bacterial strain has at least one additional copy of dxs, ispD, ispF, and idi expressed as an operon or module.

13. The bacterial strain of claim 1, having a modification that decreases expression or activity of IspB.

14. The bacterial strain of claim 1, having a deletion or inactivation of all or part of the iscR gene, and an inducible or constitutive promoter to drive expression of the genes remaining in the isc operon under conditions used for terpene or terpenoid production.

15. The bacterial strain of claim 1, wherein MEP enzyme expression or activity is altered or balanced such that 1-deoxy-D-xylulose (DOX) and/or 2-C-methyl-D-erythritol (ME) do not accumulate in the culture above about 2 g/L.

16. The bacterial strain of claim 1, comprising a mutation in glucose-6-phosphate isomerase (pgi) supporting increased terpenoid titer or MEP carbon.

17. The bacterial strain of claim 15, wherein the DOX and/or ME do not accumulate above about 1 g/L.

18. The bacterial strain of claim 1, further comprising an MEP pathway complementation comprising:
  a dxr gene; and
  ispD, ispE, and/or ispF genes.

* * * * *

SEQUENCE LISTING

<160> NUMBER OF SEQ ID NOS: 8

<210> SEQ ID NO 1

<400> SEQUENCE: 1

000

<210> SEQ ID NO 2

<400> SEQUENCE: 2

000

<210> SEQ ID NO 3
<211> LENGTH: 323

<212> TYPE: PRT
<213> ORGANISM: Escherichia coli

<400> SEQUENCE: 3

```
Met Asn Leu Glu Lys Ile Asn Glu Leu Thr Ala Gln Asp Met Ala Gly
1               5                   10                  15

Val Asn Ala Ala Ile Leu Glu Gln Leu Asn Ser Asp Val Gln Leu Ile
            20                  25                  30

Asn Gln Leu Gly Tyr Tyr Ile Val Ser Gly Gly Gly Lys Arg Ile Arg
        35                  40                  45

Pro Met Ile Ala Val Leu Ala Ala Arg Ala Val Gly Tyr Glu Gly Asn
    50                  55                  60

Ala His Val Thr Ile Ala Ala Leu Ile Glu Phe Ile His Thr Ala Thr
65                  70                  75                  80

Leu Leu His Asp Asp Val Val Asp Glu Ser Asp Met Arg Arg Gly Lys
                85                  90                  95

Ala Thr Ala Asn Ala Ala Phe Gly Asn Ala Ala Ser Val Leu Val Gly
            100                 105                 110

Asp Phe Ile Tyr Thr Arg Ala Phe Gln Met Met Thr Ser Leu Gly Ser
        115                 120                 125

Leu Lys Val Leu Glu Val Met Ser Glu Ala Val Asn Val Ile Ala Glu
    130                 135                 140

Gly Glu Val Leu Gln Leu Met Asn Val Asn Asp Pro Asp Ile Thr Glu
145                 150                 155                 160

Glu Asn Tyr Met Arg Val Ile Tyr Ser Lys Thr Ala Arg Leu Phe Glu
                165                 170                 175

Ala Ala Ala Gln Cys Ser Gly Ile Leu Ala Gly Cys Thr Pro Glu Glu
            180                 185                 190

Glu Lys Gly Leu Gln Asp Tyr Gly Arg Tyr Leu Gly Thr Ala Phe Gln
        195                 200                 205

Leu Ile Asp Asp Leu Leu Asp Tyr Asn Ala Asp Gly Glu Gln Leu Gly
    210                 215                 220

Lys Asn Val Gly Asp Asp Leu Asn Glu Gly Lys Pro Thr Leu Pro Leu
225                 230                 235                 240

Leu His Ala Met His His Gly Thr Pro Glu Gln Ala Gln Met Ile Arg
                245                 250                 255

Thr Ala Ile Glu Gln Gly Asn Gly Arg His Leu Leu Glu Pro Val Leu
            260                 265                 270

Glu Ala Met Asn Ala Cys Gly Ser Leu Glu Trp Thr Arg Gln Arg Ala
        275                 280                 285

Glu Glu Glu Ala Asp Lys Ala Ile Ala Ala Leu Gln Val Leu Pro Asp
    290                 295                 300

Thr Pro Trp Arg Glu Ala Leu Ile Gly Leu Ala His Ile Ala Val Gln
305                 310                 315                 320

Arg Asp Arg
```

<210> SEQ ID NO 4
<211> LENGTH: 398
<212> TYPE: PRT
<213> ORGANISM: Escherichia coli

<400> SEQUENCE: 4

```
Met Lys Gln Leu Thr Ile Leu Gly Ser Thr Gly Ser Ile Gly Cys Ser
1               5                   10                  15

Thr Leu Asp Val Val Arg His Asn Pro Glu His Phe Arg Val Val Ala
```

```
                         20                  25                  30
Leu Val Ala Gly Lys Asn Val Thr Arg Met Val Glu Gln Cys Leu Glu
                 35                  40                  45
Phe Ser Pro Arg Tyr Ala Val Met Asp Asp Glu Ala Ser Ala Lys Leu
 50                  55                  60
Leu Lys Thr Met Leu Gln Gln Gly Ser Arg Thr Glu Val Leu Ser
 65                  70                  75                  80
Gly Gln Gln Ala Ala Cys Asp Met Ala Ala Leu Glu Asp Val Asp Gln
                 85                  90                  95
Val Met Ala Ala Ile Val Gly Ala Ala Gly Leu Leu Pro Thr Leu Ala
                100                 105                 110
Ala Ile Arg Ala Gly Lys Thr Ile Leu Leu Ala Asn Lys Glu Ser Leu
            115                 120                 125
Val Thr Cys Gly Arg Leu Phe Met Asp Ala Val Lys Gln Ser Lys Ala
            130                 135                 140
Gln Leu Leu Pro Val Asp Ser Glu His Asn Ala Ile Phe Gln Ser Leu
145                 150                 155                 160
Pro Gln Pro Ile Gln His Asn Leu Gly Tyr Ala Asp Leu Glu Gln Asn
                165                 170                 175
Gly Val Val Ser Ile Leu Leu Thr Gly Ser Gly Gly Pro Phe Arg Glu
                180                 185                 190
Thr Pro Leu Arg Asp Leu Ala Thr Met Thr Pro Asp Gln Ala Cys Arg
                195                 200                 205
His Pro Asn Trp Ser Met Gly Arg Lys Ile Ser Val Asp Ser Ala Thr
            210                 215                 220
Met Met Asn Lys Gly Leu Glu Tyr Ile Glu Ala Arg Trp Leu Phe Asn
225                 230                 235                 240
Ala Ser Ala Ser Gln Met Glu Val Leu Ile His Pro Gln Ser Val Ile
                245                 250                 255
His Ser Met Val Arg Tyr Gln Asp Gly Ser Val Leu Ala Gln Leu Gly
                260                 265                 270
Glu Pro Asp Met Arg Thr Pro Ile Ala His Thr Met Ala Trp Pro Asn
            275                 280                 285
Arg Val Asn Ser Gly Val Lys Pro Leu Asp Phe Cys Lys Leu Ser Ala
            290                 295                 300
Leu Thr Phe Ala Ala Pro Asp Tyr Asp Arg Tyr Pro Cys Leu Lys Leu
305                 310                 315                 320
Ala Met Glu Ala Phe Glu Gln Gly Gln Ala Ala Thr Thr Ala Leu Asn
                325                 330                 335
Ala Ala Asn Glu Ile Thr Val Ala Ala Phe Leu Ala Gln Gln Ile Arg
            340                 345                 350
Phe Thr Asp Ile Ala Ala Leu Asn Leu Ser Val Leu Glu Lys Met Asp
            355                 360                 365
Met Arg Glu Pro Gln Cys Val Asp Asp Val Leu Ser Val Asp Ala Asn
 370                 375                 380
Ala Arg Glu Val Ala Arg Lys Glu Val Met Arg Leu Ala Ser
385                 390                 395

<210> SEQ ID NO 5
<211> LENGTH: 372
<212> TYPE: PRT
<213> ORGANISM: Escherichia coli

<400> SEQUENCE: 5
```

```
Met His Asn Gln Ala Pro Ile Gln Arg Arg Lys Ser Thr Arg Ile Tyr
1               5                   10                  15

Val Gly Asn Val Pro Ile Gly Asp Gly Ala Pro Ile Ala Val Gln Ser
            20                  25                  30

Met Thr Asn Thr Arg Thr Thr Asp Val Glu Ala Thr Val Asn Gln Ile
        35                  40                  45

Lys Ala Leu Glu Arg Val Gly Ala Asp Ile Val Arg Val Ser Val Pro
50                  55                  60

Thr Met Asp Ala Ala Glu Ala Phe Lys Leu Ile Lys Gln Gln Val Asn
65                  70                  75                  80

Val Pro Leu Val Ala Asp Ile His Phe Asp Tyr Arg Ile Ala Leu Lys
                85                  90                  95

Val Ala Glu Tyr Gly Val Asp Cys Leu Arg Ile Asn Pro Gly Asn Ile
            100                 105                 110

Gly Asn Glu Glu Arg Ile Arg Met Val Val Asp Cys Ala Arg Asp Lys
        115                 120                 125

Asn Ile Pro Ile Arg Ile Gly Val Asn Ala Gly Ser Leu Glu Lys Asp
130                 135                 140

Leu Gln Glu Lys Tyr Gly Glu Pro Thr Pro Gln Ala Leu Leu Glu Ser
145                 150                 155                 160

Ala Met Arg His Val Asp His Leu Asp Arg Leu Asn Phe Asp Gln Phe
                165                 170                 175

Lys Val Ser Val Lys Ala Ser Asp Val Phe Leu Ala Val Glu Ser Tyr
            180                 185                 190

Arg Leu Leu Ala Lys Gln Ile Asp Gln Pro Leu His Leu Gly Ile Thr
        195                 200                 205

Glu Ala Gly Gly Ala Arg Ser Gly Ala Val Lys Ser Ala Ile Gly Leu
210                 215                 220

Gly Leu Leu Leu Ser Glu Gly Ile Gly Asp Thr Leu Arg Val Ser Leu
225                 230                 235                 240

Ala Ala Asp Pro Val Glu Glu Ile Lys Val Gly Phe Asp Ile Leu Lys
                245                 250                 255

Ser Leu Arg Ile Arg Ser Arg Gly Ile Asn Phe Ile Ala Cys Pro Thr
            260                 265                 270

Cys Ser Arg Gln Glu Phe Asp Val Ile Gly Thr Val Asn Ala Leu Glu
        275                 280                 285

Gln Arg Leu Glu Asp Ile Ile Thr Pro Met Asp Val Ser Ile Ile Gly
290                 295                 300

Cys Val Val Asn Gly Pro Gly Glu Ala Leu Val Ser Thr Leu Gly Val
305                 310                 315                 320

Thr Gly Asn Lys Lys Ser Gly Leu Tyr Glu Asp Gly Val Arg Lys
                325                 330                 335

Asp Arg Leu Asp Asn Asn Asp Met Ile Asp Gln Leu Glu Ala Arg Ile
        340                 345                 350

Arg Ala Lys Ala Ser Gln Leu Asp Glu Ala Arg Arg Ile Asp Val Gln
355                 360                 365

Gln Val Glu Lys
        370

<210> SEQ ID NO 6
<211> LENGTH: 316
<212> TYPE: PRT
<213> ORGANISM: Escherichia coli

<400> SEQUENCE: 6
```

```
Met Gln Ile Leu Leu Ala Asn Pro Arg Gly Phe Cys Ala Gly Val Asp
1               5                   10                  15

Arg Ala Ile Ser Ile Val Glu Asn Ala Leu Ala Ile Tyr Gly Ala Pro
            20                  25                  30

Ile Tyr Val Arg His Glu Val His Asn Arg Tyr Val Val Asp Ser
        35                  40                  45

Leu Arg Glu Arg Gly Ala Ile Phe Ile Glu Gln Ile Ser Glu Val Pro
    50                  55                  60

Asp Gly Ala Ile Leu Ile Phe Ser Ala His Gly Val Ser Gln Ala Val
65                  70                  75                  80

Arg Asn Glu Ala Lys Ser Arg Asp Leu Thr Val Phe Asp Ala Thr Cys
                85                  90                  95

Pro Leu Val Thr Lys Val His Met Glu Val Ala Arg Ala Ser Arg Arg
                100                 105                 110

Gly Glu Glu Ser Ile Leu Ile Gly His Ala Gly His Pro Glu Val Glu
            115                 120                 125

Gly Thr Met Gly Gln Tyr Ser Asn Pro Glu Gly Gly Met Tyr Leu Val
130                 135                 140

Glu Ser Pro Asp Asp Val Trp Lys Leu Thr Val Lys Asn Glu Glu Lys
145                 150                 155                 160

Leu Ser Phe Met Thr Gln Thr Thr Leu Ser Val Asp Asp Thr Ser Asp
                165                 170                 175

Val Ile Asp Ala Leu Arg Lys Arg Phe Pro Lys Ile Val Gly Pro Arg
            180                 185                 190

Lys Asp Asp Ile Cys Tyr Ala Thr Thr Asn Arg Gln Glu Ala Val Arg
            195                 200                 205

Ala Leu Ala Glu Gln Ala Glu Val Val Leu Val Gly Ser Lys Asn
210                 215                 220

Ser Ser Asn Ser Asn Arg Leu Ala Glu Leu Ala Gln Arg Met Gly Lys
225                 230                 235                 240

Arg Ala Phe Leu Ile Asp Asp Ala Lys Asp Ile Gln Glu Glu Trp Val
                245                 250                 255

Lys Glu Val Lys Cys Val Gly Val Thr Ala Gly Ala Ser Ala Pro Asp
                260                 265                 270

Ile Leu Val Gln Asn Val Ala Arg Leu Gln Gln Leu Gly Gly Gly
            275                 280                 285

Glu Ala Ile Pro Leu Glu Gly Arg Glu Asn Ile Val Phe Glu Val
    290                 295                 300

Pro Lys Glu Leu Arg Val Asp Ile Arg Glu Val Asp
305                 310                 315

<210> SEQ ID NO 7
<211> LENGTH: 438
<212> TYPE: PRT
<213> ORGANISM: Brucella abortus

<400> SEQUENCE: 7

Met Thr Thr Asn Val Ala Leu Val Gly Leu Ala Arg Asp Leu Ala Ala
1               5                   10                  15

Arg Ala Glu Thr Gly Lys Pro Ile Arg Ile Gly Leu Ile Gly Ala Gly
            20                  25                  30

Glu Met Gly Thr Asp Ile Val Thr Gln Val Ala Arg Met Gln Gly Ile
            35                  40                  45

Glu Val Gly Ala Leu Ser Ala Arg Arg Leu Pro Asn Thr Phe Lys Ala
```

```
            50                  55                  60
Ile Arg Thr Ala Tyr Gly Asp Glu Glu Asn Ala Arg Glu Ala Thr Thr
 65                  70                  75                  80

Glu Ser Ala Met Thr Arg Ala Ile Glu Ala Gly Lys Ile Ala Val Thr
                 85                  90                  95

Asp Asp Asn Asp Leu Ile Leu Ser Asn Pro Leu Ile Asp Val Ile Ile
            100                 105                 110

Asp Ala Thr Gly Ile Pro Glu Val Gly Ala Glu Thr Gly Ile Ala Ala
            115                 120                 125

Ile Arg Asn Gly Lys His Leu Val Met Met Asn Val Glu Ala Asp Val
        130                 135                 140

Thr Ile Gly Pro Tyr Leu Lys Ala Gln Ala Asp Lys Gln Gly Val Ile
145                 150                 155                 160

Tyr Ser Leu Gly Ala Gly Asp Glu Pro Ser Ser Cys Met Glu Leu Ile
                165                 170                 175

Glu Phe Val Ser Ala Leu Gly Tyr Glu Val Val Ser Ala Gly Lys Gly
            180                 185                 190

Lys Asn Asn Pro Leu Asn Phe Asp Ala Thr Pro Asp Asp Tyr Arg Gln
        195                 200                 205

Glu Ala Asp Arg Arg Asn Met Asn Val Arg Leu Leu Val Glu Phe Ile
210                 215                 220

Asp Gly Ser Lys Thr Met Val Glu Met Ala Ala Ile Ala Asn Ala Thr
225                 230                 235                 240

Gly Leu Val Pro Asp Ile Ala Gly Met His Gly Pro Arg Ala Ser Ile
                245                 250                 255

Asp Gln Leu Ser His Thr Leu Ile Pro Gln Ala Glu Gly Gly Val Leu
            260                 265                 270

Ser Lys Ser Gly Val Val Asp Tyr Ser Ile Gly Lys Gly Val Ser Pro
        275                 280                 285

Gly Val Phe Val Val Ala Lys Met Asp His Pro Arg Leu Asn Glu Arg
290                 295                 300

Leu Glu Asp Leu Lys Ile Gly Lys Gly Pro Tyr Phe Thr Phe His Arg
305                 310                 315                 320

Pro Tyr His Leu Thr Ser Leu Glu Val Pro Leu Thr Val Ala Arg Val
                325                 330                 335

Val Leu His Gly Lys Thr Asp Met Val Pro Leu Pro Lys Pro Val Ala
            340                 345                 350

Glu Val Cys Ala Val Ala Lys Lys Asp Met Gln Pro Gly Glu His Leu
        355                 360                 365

Asp Ala Ile Gly Gln Tyr Cys Tyr Arg Ser Trp Ile Met Thr Val Pro
370                 375                 380

Glu Ala Arg Ala Ala Lys Ala Ile Pro Cys Gly Leu Leu Gln Asn Gly
385                 390                 395                 400

Thr Val Ile Ala Pro Ile Lys Lys Gly Glu Leu Ile Thr Tyr Ala Asn
                405                 410                 415

Ala Ala Pro Gln Pro Gly Ser Arg Ile Ala Glu Leu Arg Ala Leu Gln
            420                 425                 430

Asp Ala Met Leu Gly Gln
            435

<210> SEQ ID NO 8
<211> LENGTH: 283
<212> TYPE: PRT
<213> ORGANISM: Escherichia coli
```

```
<400> SEQUENCE: 8

Met Arg Thr Gln Trp Pro Ser Pro Ala Lys Leu Asn Leu Phe Leu Tyr
1               5                   10                  15

Ile Thr Gly Gln Arg Ala Asp Gly Tyr His Thr Leu Gln Thr Leu Phe
            20                  25                  30

Gln Phe Leu Asp Tyr Gly Asp Thr Ile Ser Ile Glu Leu Arg Asp Asp
            35                  40                  45

Gly Asp Ile Arg Leu Leu Thr Pro Val Glu Gly Val Glu His Glu Asp
50                      55                  60

Asn Leu Ile Val Arg Ala Ala Arg Leu Leu Met Lys Thr Ala Ala Asp
65                  70                  75                  80

Ser Gly Arg Leu Pro Thr Gly Ser Gly Ala Asn Ile Ser Ile Asp Lys
                85                  90                  95

Arg Leu Pro Met Gly Gly Gly Leu Gly Gly Ser Ser Asn Ala Ala
                100                 105                 110

Thr Val Leu Val Ala Leu Asn His Leu Trp Gln Cys Gly Leu Ser Met
            115                 120                 125

Asp Glu Leu Ala Glu Met Gly Leu Thr Leu Gly Ala Asp Val Pro Val
        130                 135                 140

Phe Val Arg Gly His Ala Ala Phe Ala Glu Gly Val Gly Glu Ile Leu
145                 150                 155                 160

Thr Pro Val Asp Pro Pro Glu Lys Trp Tyr Leu Val Ala His Pro Gly
                165                 170                 175

Val Ser Ile Pro Thr Pro Val Ile Phe Lys Asp Pro Glu Leu Pro Arg
            180                 185                 190

Asn Thr Pro Lys Arg Ser Ile Glu Thr Leu Leu Lys Cys Glu Phe Ser
        195                 200                 205

Asn Asp Cys Glu Val Ile Ala Arg Lys Arg Phe Arg Glu Val Asp Ala
        210                 215                 220

Val Leu Ser Trp Leu Leu Glu Tyr Ala Pro Ser Arg Leu Thr Gly Thr
225                 230                 235                 240

Gly Ala Cys Val Phe Ala Glu Phe Asp Thr Glu Ser Glu Ala Arg Gln
                245                 250                 255

Val Leu Glu Gln Ala Pro Glu Trp Leu Asn Gly Phe Val Ala Lys Gly
            260                 265                 270

Ala Asn Leu Ser Pro Leu His Arg Ala Met Leu
            275                 280
```